US009994878B2

(12) United States Patent
Koepke et al.

(10) Patent No.: US 9,994,878 B2
(45) Date of Patent: Jun. 12, 2018

(54) RECOMBINANT MICROORGANISMS AND USES THEREFOR

(71) Applicant: LanzaTech New Zealand Limited, Auckland (NZ)

(72) Inventors: Michael Koepke, Auckland (NZ); Wendy Yiting Chen, Auckland (NZ)

(73) Assignee: LanzaTech New Zealand Limited, Auckland (NZ)

( * ) Notice: Subject to any disclaimer, the term of this patent is extended or adjusted under 35 U.S.C. 154(b) by 247 days.

(21) Appl. No.: 13/905,143

(22) Filed: May 30, 2013

(65) Prior Publication Data

US 2013/0323806 A1 Dec. 5, 2013

Related U.S. Application Data

(60) Provisional application No. 61/653,348, filed on May 30, 2012.

(51) Int. Cl.
*C12P 7/52* (2006.01)
*C12R 1/145* (2006.01)
*C12N 9/02* (2006.01)
*C12P 7/42* (2006.01)

(52) U.S. Cl.
CPC ............... *C12P 7/52* (2013.01); *C12N 9/0008* (2013.01); *C12P 7/42* (2013.01); *C12R 1/145* (2013.01); *C12Y 102/01075* (2013.01)

(58) Field of Classification Search
CPC . C12P 7/52; C12P 7/42; C12N 9/0008; C12Y 102/01075; C12R 1/145
See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy et al. | |
| 6,368,819 B1 | 4/2002 | Gaddy et al. | |
| 7,186,541 B2 * | 3/2007 | Gokarn ............... | C12N 9/0004 435/232 |
| 2011/0003344 A1 * | 1/2011 | Burk ................... | C12N 9/0008 435/92 |
| 2011/0008861 A1 * | 1/2011 | Berry .................. | C12N 1/20 435/161 |
| 2011/0125118 A1 | 5/2011 | Lynch | |
| 2011/0129904 A1 * | 6/2011 | Burgard .............. | C12N 15/52 435/252.33 |
| 2011/0177564 A1 * | 7/2011 | Stephanopoulos ... | C12M 23/58 435/101 |
| 2011/0201068 A1 * | 8/2011 | Pharkya .............. | C12N 15/52 435/136 |
| 2011/0229947 A1 | 9/2011 | Zahn et al. | |
| 2012/0041232 A1 | 2/2012 | Lynch | |
| 2012/0064622 A1 * | 3/2012 | Fischer et al. ........... | 435/348 |
| 2012/0077236 A1 * | 3/2012 | Gokarn ............... | C12N 9/0004 435/135 |
| 2012/0135481 A1 * | 5/2012 | Jessen ................ | C12N 1/18 435/141 |
| 2013/0288317 A1 * | 10/2013 | Ramseier .............. | C12P 7/625 435/135 |
| 2013/0323766 A1 * | 12/2013 | Sillers ................ | C12N 1/22 435/15 |

FOREIGN PATENT DOCUMENTS

| | | |
|---|---|---|
| JP | 201285635 | 5/2012 |
| WO | WO2002-08438 | 1/2002 |
| WO | WO2008-028055 | 3/2008 |
| WO | WO2009-064200 | 5/2009 |
| WO | WO2009089457 | 7/2009 |
| WO | WO2009111513 | 9/2009 |
| WO | 2012019175 A2 | 2/2012 |
| WO | WO2012-115527 | 8/2012 |

OTHER PUBLICATIONS

Menendez, C., et al., 1999, "Presence of acetyl coenzyme A (CoA) carboxylase and propionyl-CoA carboxylase in autotrophic Crenarchaeota and indication for operation of a 3-hydroxypropionate cycle in autotrophic carbon fixation", Journal of Bacteriology, vol. 181, No. 4, pp. 1088-1098.*
Hugler M., et al., 2002, "Malonyl-coenzyme A reductase from Chloroflexus aurantiacus, a key enzyme of the 3-hydroxypropionate cycle for autotrophic CO(2) fixation", Journal of Bacteriology, vol. 184, pp. 2404-2410.*
Zarzycki, J., et al., 2011, "Coassimilation of organic substrates via the autotrophic 3-hydroxypropionate bi-cycle in Chloroflexus aurantiacus", Applied and Environmental Microbiology, vol. 77, No. 17, pp. 6181-6188.*
Tang K.H., et al., 2011, "Complete genome sequence of the filamentous anoxygenic phototrophic bacterium Chloroflexus aurantiacus", BMC Genomics, vol. 12, pp. 334-334.*
NCBI Reference Sequence: YP_001636995.1,acetyl-CoA carboxylase, biotin carboxylase [Chloroflexus aurantiacus J-10-fl], initial submission on Dec. 5, 2007 by Copeland, A., et al., US DOE Joint Genome Institute, 2800.*
Tang, K.H., et al., 2011, ."Complete genome sequence of the filamentous anoxygenic phototrophic bacterium Chloroflexus aurantiacus", BMC Genomics 2011, 12:334 [as PDF].*

(Continued)

*Primary Examiner* — Kagnew H Gebreyesus
(74) *Attorney, Agent, or Firm* — Andrea Schoen

(57) ABSTRACT

Bacteria are genetically engineered to produce 3-hydroxypropionate (3-HP). The bacteria are carboxydotrophic acetogens. The bacteria produce acetyl-coA using the Wood-Ljungdahl pathway for fixing $CO/CO_2$. A malonyl-coA reductase from a bacterium that contains such an enzyme is introduced. Additionally, an acetyl-coA carboxylase may also be introduced The production of 3-HP can be improved by overproduction of acetyl-CoA carboxylase or by overproduction of biotin. This can be effected by improved promoters or higher copy number or enzymes that are catalytically more efficient.

13 Claims, 1 Drawing Sheet

(56) References Cited

OTHER PUBLICATIONS

Munasinghe et al. Biomass-derived syngas fermentation into biofuels: Opportunities and challenges., Bioresource Technology (2010), vol. 101, Issue 13, pp. 5013-5022.*

Alber, Birgit et al, Malonyl-Coenzyme A reductase in the modified 3-hydroxypropionate cycle for autotrophic carbon fixation in Archaeal Metallosphaera and Sulfolobus supp, Dec. 2006, vol. 188, No. 24, pp. 8551-8559.

Abrini, J., Naveau, H., & Nyns, E. J. *Clostridium autoethanogenum*, sp. nov., an anaerobic bacterium that produces ethanol from carbon monoxide. Archives of microbiology, 161(4), 345-351(1994).

Collins, M. D., Lawson, P. A., Willems, A., Cordoba, J. J., Fernandez-Garayzabal, J., Garcia, P., Cai, J., et al. The phylogeny of the genus Clostridium: proposal of five new genera and eleven new species combinations. International journal of systematic bacteriology, 44(4), 812-26(1994).

Herbert, M., O'Keeffe, T.A., Purdy, D., Elmore, M., & Minton, N. P. Gene transfer into Clostridium difficile CD630 and characterisation of its methylase genes. FEMS Microbiology Letters, 229(1), 103-110(2003).

Jennert, K. C., Tardif, C., Young, D. I., & Young, M. Gene transfer to Clostridium cellulolyticum ATCC 35319. Microbiology (Reading, England), 146 Pt 12, 3071-80(2000).

Kita, A., Iwasaki, Y., Sakai, S., Okuto, S., Takaoka, K., Suzuki, T., Yano, S., et al. Development of genetic transformation and heterologous expression system in carboxydotrophic thermophilic acetogen Moorella thermoacetica. Journal of Bioscience and Bioengineering, vol. 115 (4) pp. 347-352 (2013).

Köpke, M., Held, C., Hujer, S., Liesegang, H., Wiezer, A., Wollherr, A., Ehrenreich, A., et al. Clostridium ijungdahlii represents a microbial production platform based on syngas. Proceedings of the National Academy of Sciences of the United States of America, 107(29)(2010).

Köpke, M., Mihalcea, C., Liew, F., Tizard, J. H., Ali, M. S., Conolly, J. J., Al-Sinawi, B., et al. 2,3-Butanediol Production by Acetogenic Bacteria, an Alternative Route to Chemical Synthesis, Using Industrial Waste Gas. Applied and environmental microbiology, 77(15), 5467-75(2011).

Leang, C., Ueki, T., Nevin, K. P., & Lovley, D. R. A Genetic System for Clostridium ijungdahlii: A Chassis for Autotrophic Production of Biocommodities and a Model Homoacetogen. Applied and environmental microbiology, (Nov. 2012).

Mermelstein, L. D., Welker, N. E., Bennett, G. N., & Papoutsakis, E. T. Expression of cloned homologous fermentative genes in Clostridium acetobutylicum ATCC 824. Bio/technology (Nature Publishing Company), 10(2), 190-195(1992).

Perez, J. M., Richter, H., Loftus, S. E., & Angenent, L. T. Biocatalytic reduction of short-chain carboxylic acids into their corresponding alcohols with syngas fermentation. Biotechnology and bioengineering, 1-30(2012).

Strätz, M., Sauer, U., Kuhn, a, & Dürre, P. Plasmid Transfer into the Homoacetogen Acetobacterium woodii by Electroporation and Conjugation. Applied and environmental microbiology, 60(3), 1033-7(1994).

Tanner, R. S., Miller, L. M., & Yang, D. *Clostridium ijungdahlii* sp. nov., an acetogenic species in clostridial rRNA homology group I. International journal of systematic bacteriology, 43(2), 232(1993).

Tyurin, Michael, & Kiriukhin, M. Electrofusion of cells of Acetogen *Clostridium* sp. MT 351 with erm (B) or cat in the chromosome. Journal of Biotech, 1-12(2012).

Tyurin, MV, Desai, S., & Lynd, L. Electrotransformation of Clostridium thermocellum. Applied and environmental mictrobiology 70(2), 883-890(2004).

Williams, D. R., Young, D. I., & Young, M. Conjugative plasmid transfer from *Escherichia coli* to Clostridium acetobutylicum. Journal of general microbiology, 136(5), 819-26(1990).

Tirado-Acevedo O. Production of Bioethanol from Synthesis Gas Using Clostridium ijungdahlii. PhD thesis, North Carolina State University, 2010.

Murray, N.E. et al. (2000) Microbial. Molec. Biol. Rev. 64, 412.

Köpke & Dürre, Biochemical production of biobutanol, in: Handbook of biofuels production: processes and technologies (Eds.: Luque, Campelo & Clark), Woodhead Publishing Ltd, Camebridge, UK: 221-257 (2011).

Ismail et al., J. Bacteriol, 1993, 175: 5079-5105.

Berg, Appl Environ Microbiol, 77: 1925-1936, 2011.

Agarkar, Production of 3-hydroxypropionate from biomass, Iowa State University, Thesis, 2007.

Zhang, Construction of a recombinant *E. coli* could produce 3-hydroxypropionic acid via 3-hydroxypropionic acid pathway, Beijing Science and Technology University, Thesis, 2009.

Chinese Patent Application No. 2013800407933, Chinese Patent Office, Office Action dated Aug. 22, 2016.

Office Action, Japanese Patent Application No. 2015-514947, Japanese Patent Office, Mar. 21, 2017.

Ohshima, Bulletin of Kyoto University of Education, Ser, B, Nos. 71/72, pp. 17-21, 1998.

* cited by examiner

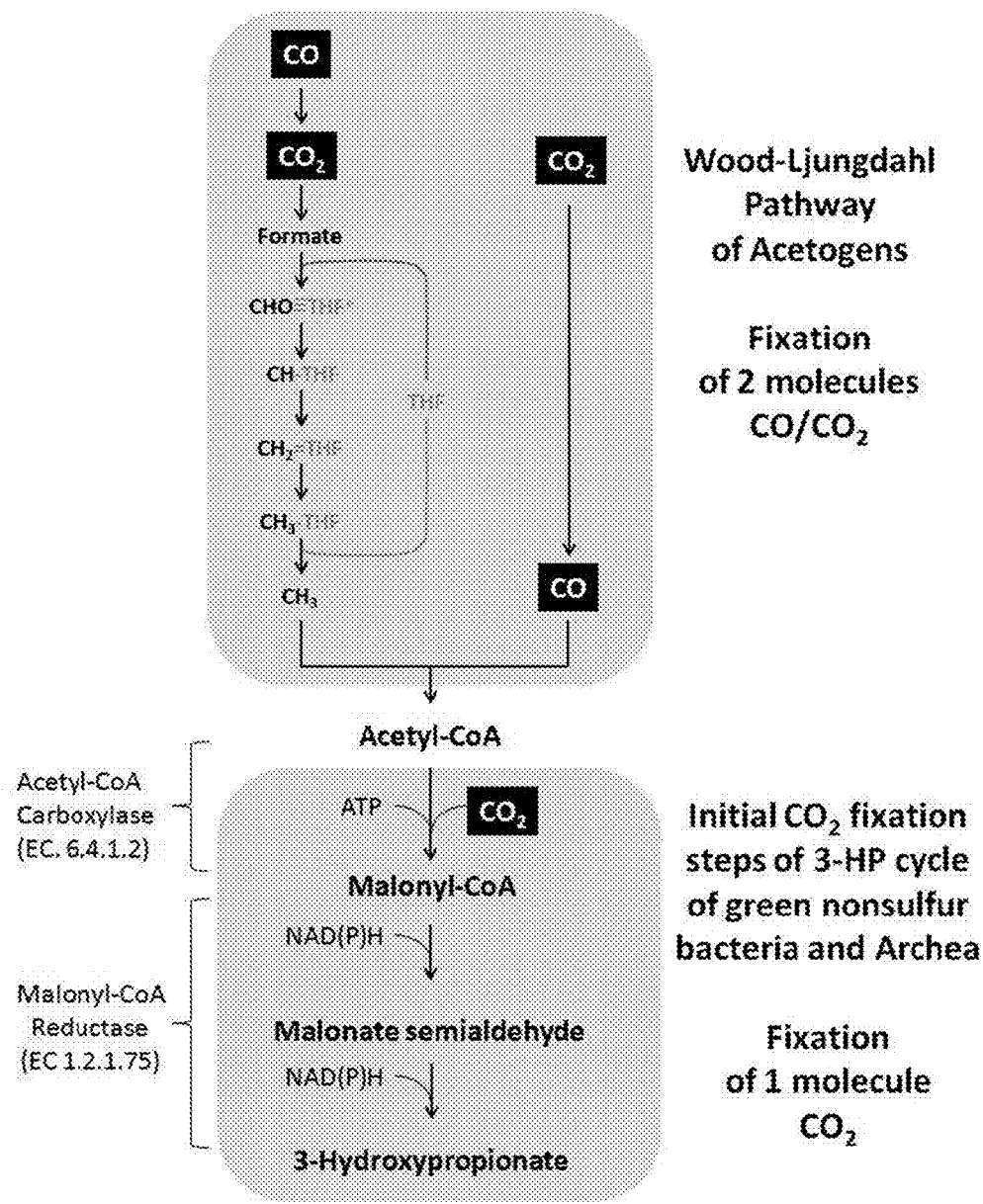

SEQUENCE LISTING

<160> NUMBER OF SEQ ID NOS: 26

<210> SEQ ID NO 1
<211> LENGTH: 3660
<212> TYPE: DNA
<213> ORGANISM: Cloroflexus auranticus

<400> SEQUENCE: 1

```
atgtcaggaa caggtagatt agctggaaaa attgcattaa ttacaggtgg tgctggtaat      60
ataggatcag aattaactag aagatttctt gctgaaggtg caactgttat tatatcaggt     120
agaaatagag caaaacttac tgcattagca gagagaatgc aagcagaagc aggtgttcca     180
```

```
gcaaaaagaa ttgatcttga agtaatggat ggttcagatc ctgttgcagt tagagctgga      240
atagaagcta ttgttgctag acatggacag atagatatat tagttaataa tgctggaagt      300
gctggtgcac agagaagatt agctgaaatt ccacttactg aagcagaatt aggaccaggt      360
gcagaagaga ctcttcatgc ttctatagct aatttattag gtatgggttg gcatttaatg      420
agaatagctg caccacacat gcctgttgga agtgcagtaa taaatgtttc aactatattt      480
tcaagagcta atattatgg tagaataacct tacgtaacac ctaaagctgc acttaatgca      540 cttttctcaat tagcagcaag agaacttggt gctagaggta taagagtaaa cacaatattt      600
cctggaccaa tagagtcaga tagaattaga acagtatttc agagaatgga tcaacttaaa      660
ggaagacctg aaggtgatac agctcatcat tttcttaata ctatgagact ttgtagagca      720
aatgatcaag gtgcattaga gagaagattt ccaagtgttg gtgatgtagc agacgctgct      780
gtatttttag ctagtgctga atcagcagca ttatcaggtg aaacaattga agtaactcat      840
ggtatggaat taccagcttg ttcagagact tctttattag caagaactga cttaagaact      900
atagatgctt caggtagaac aactcttata tgtgctggtg atcaaattga agaagtaatg      960
gctttaacag gaatgttaag aacttgcgga tctgaagtaa ttataggatt tagatcagct     1020
gcagcattag cacagtttga gcaggcagta atgaatccta aagacttgc aggtgcagat     1080 ttcactccac ctatagcatt accacttgac ccaagagatc cagctactat agatgctgta     1140
tttgattggg ctggtgaaaa tacaggtggt atacatgcag cagtaatatt acctgcaact     1200
agtcatgaac cagcaccatg tgttattgaa gttgatgatg agagagtact taactttta     1260 gctgatgaaa taacaggaac aattgtaata gcaagtagac ttgcaagata ttggcaatct     1320
cagagactta caccaggtgc tagagcaaga ggtccaagag taattttct tagtaatggt     1380 gctgatcaga atggaaatgt atatggtaga atacagtcag ctgcaattgg acaattaata     1440
agagtttgga gacatgaggc tgaacttgat tatcaaagag cttcagcagc tggtgaccat     1500
gttcttccac ctgtatgggc aaatcagatt gtaagatttg ctaatagaag tcttgaaggt     1560 cttgaattg cttgtgcttg gactgctcaa cttttacatt ctcaaagaca cataaatgaa      1620
ataactttaa atataccagc aaacattagt gcaactacag gtgcaagatc agctagtgtt     1680
ggttgggctg aatcttaat tggacttcat ttaggaaagg tagctcttat aacaggtggt     1740
tcagctggaa taggtggtca ataggaaga ctttagcac ttagtggtgc tagagtaatg      1800
cttgctgcaa gagatagaca caaattagaa caaatgcaag caatgattca gagtgaactt     1860
gcagaagttg gatatactga tgttgaagac agagttcata tagctcctgg atgtgatgta     1920
agttctgaag ctcagttagc agatcttgtt gagagaactt tatctgcatt cggaacagtt     1980
gattatctta taaataatgc aggtatagca ggtgttgaag aaatggttat agatatgcct     2040
gtagaaggtt ggagacatac actttttgct aaccttatat caaactattc tttaatgaga     2100
aaattagctc cacttatgaa aaagcaagga agtggttata tacttaatgt atcatcatat     2160
ttcggtggtg aaaagatgc agctatacca tacccaaata gagcagatta tgctgtaagt     2220
aaagcaggac agagagctat ggctgaagta tttgctagat tcttaggacc agaaaattcag     2280 attaatgcta tagcaccagg accagtgaaa ggtgacagac ttagaggtac tggtgaaaga     2340
cctggacttt ttgctagaag agctagatta atacttgaaa ataagagact taatgagctt     2400
catgctgctt taatagctgc tgctagaaca gatgagagat caatgcatga acttgtagaa     2460
cttttattac caaatgacgt agcagcatta gagcaaaacc cagcagctcc tacagctctt     2520
agagaacttg ctagaagatt tagatcagaa ggtgatcctg ctgcaagttc ttctagtgca     2580
```

```
cttttaaaata gaagtatagc tgcaaaactt ttagcaagat tacataacgg tggttatgta    2640
ttacctgctg atatattcgc aaatttacca aaccctccag atcctttctt tactagagca    2700
caaatagaca gagaagcaag aaaagtaaga gatggaatta tgggaatgct ttatttacaa    2760
agaatgccaa ctgagtttga cgttgcaatg gctactgtat attatttagc agatagaaat    2820
gtttctggtg aaacttttca tccatcaggt ggtttaagat acgaaagaac acctacaggt    2880
ggtgaattat tcggacttcc ttctccagaa agacttgcag aattagtagg atcaacagtt    2940
tatcttatag gtgaacattt aactgagcac cttaatttac ttgctagagc atatcttgaa    3000
agatatggtg caagacaagt agttatgata gtagagacag agactggtgc agaaacaatg    3060
agaagattac ttcatgatca cgttgaagct ggtagattaa tgactattgt agcaggtgat    3120
cagatagaag ctgctattga tcaagctatt acaagatatg gtagaccagg acctgttgta    3180
tgtactcctt ttagacctct tcctactgtt ccattagtag gtagaaagga ttctgactgg    3240
tcaacagttt taagtgaagc agaatttgct gagttatgcg aacatcaatt aacacatcac    3300
tttagagttg ctagaaagat agctttatca gatggtgcat ctttagcatt agtaactcca    3360
gagactactg caactagtac aactgaacaa ttcgcattag ctaattttat aaagacaaca    3420
ttacacgctt ttactgctac aattggtgta gaaagtgaaa gaactgcaca agaattta    3480 attaaccagg ttgatttaac aagaagagca agagctgaag aacctagaga tcctcatgag    3540
agacaacaag agcttgaaag attttatagaa gctgttcttc ttgttacagc accttttacct    3600 ccagaagcag atactagata cgcaggtaga atacatagag gtagagcaat aacagtataa   3660

<210> SEQ ID NO 2
<211> LENGTH: 479
<212> TYPE: DNA
<213> ORGANISM: Clostridium autoethanogenum

<400> SEQUENCE: 2
aatatgatat ttatgtccat tgtgaaaggg attatattca actattattc cagttacgtt      60
catagaaatt ttcctttcta aaatatttta ttccatgtca agaactctgt ttatttcatt     120
aaagaactat aagtacaaag tataaggcat ttgaaaaaat aggctagtat attgattgat     180
tatttatttt aaaatgccta agtgaaatat atacatatta taacaataaa ataagtatta     240
gtgtaggatt tttaaataga gtatctattt tcagattaaa tttttgatta tttgatttac     300
attatataat attgagtaaa gtattgacta gcaaaatttt ttgatacttt aatttgtgaa     360
atttcttatc aaaagttata ttttttgaata attttttattg aaaaatacaa ctaaaaagga    420
ttatagtata agtgtgtgta attttgtgtt aaatttaaag ggaggaaatg aacatgaaa      479

<210> SEQ ID NO 3
<211> LENGTH: 3552
<212> TYPE: DNA
<213> ORGANISM: Artificial Sequence
<220> FEATURE:
<223> OTHER INFORMATION: plasmid pMTL 85245

<400> SEQUENCE: 3
aaactccttt ttgataatct catgaccaaa atcccttaac gtgagttttc gttccactga      60
gcgtcagacc ccgtagaaaa gatcaaagga tcttcttgag atccttttt tctgcgcgta     120 atctgctgct tgcaaacaaa aaaccaccg ctaccagcgg tggtttgttt gccggatcaa      180
gagctaccaa ctctttttcc gaaggtaact ggcttcagca gagcgcagat accaaatact     240
```

```
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600 ctttatagtc ctgtcgggtt tcgccacctc tgacttgagc gtcgattttt gtgatgctcg    660 tcagggggc ggagcctatg gaaaaacgcc agcaacgcgg ccttttacg gttcctggcc      720 ttttgctggc cttttgctca catgttcttt cctgcgttat ccctgattc tgtggataac     780 cgtattaccg cctttgagtg agctgatacc gctcgccgca gccgaacgac cgagcgcagc   840
gagtcagtga gcgaggaagc ggaagagcgc ccaatacgca gggcccctg caggataaaa    900 aaattgtaga taaattttat aaatagttt tatctacaat ttttttatca ggaaacagct    960
atgaccgcgg ccgcaatatg atatttatgt ccattgtgaa aggattata ttcaactatt   1020 attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gattttttaaa tagagtatct attttcagat taaattttttg  1260 attatttgat ttacattata taatattgag taaagtattg actagcaaaa ttttttgata   1320
ctttaatttg tgaaatttct tatcaaaagt tatattttttg aataatttt attgaaaaat   1380 acaactaaaa aggattatag tataagtgtg tgtaattttg tgttaaattt aagggagga    1440 aatgaacatg aaacatatgg tgaccatgat tacgaattcg agctcggtac ccggggatcc   1500
tctagagtcg acgtcacgcg tccatggaga tctcgaggcc tgcagacatg caagcttggc   1560
actggccgtc gttttacaac gtcgtgactg ggaaaaccct ggcgttaccc aacttaatcg   1620
ccttgcagca catcccccctt tcgccagctg gcgtaatagc gaagaggccc gcaccgatcg   1680
cccttcccaa cagttgcgca gcctgaatgg cgaatggcgc tagcataaaa ataagaagcc   1740
tgcatttgca ggcttcttat ttttatggcg cgccgcattc acttcttttc tatataaata   1800
tgagcgaagc gaataagcgt cggaaaagca gcaaaaagtt tccttttttgc tgttggagca   1860 tggggggttca gggggtgcag tatctgacgt caatgccgag cgaaagcgag ccgaagggta   1920
gcatttacgt tagataaccc cctgatatgc tccgacgctt tatatagaaa agaagattca   1980
actaggtaaa atcttaatat aggttgagat gataaggttt ataaggaatt tgtttgttct   2040 aattttttcac tcattttgtt ctaatttctt ttaacaaatg ttcttttttt tttagaacag   2100
ttatgatata gttagaatag tttaaaataa ggagtgagaa aaagatgaaa gaaagatatg   2160
gaacagtcta taaggctct cagaggctca tagacgaaga aagtggagaa gtcatagagg    2220
tagacaagtt ataccgtaaa caaacgtctg gtaacttcgt aaaggcatat atagtgcaat    2280
taataagtat gttagatatg attggcggaa aaaaacttaa aatcgttaac tatatcctag   2340
ataatgtcca cttaagtaac aatacaatga tagctacaac aagagaaata gcaaaagcta   2400
caggaacaag tctacaaaca gtaataacaa cacttaaaat cttagaagaa ggaaatatta   2460 taaaagaaa aactggagta ttaatgttaa accctgaact actaatgaga ggcgacgacc    2520
aaaaacaaaa atacctctta ctcgaatttg ggaactttga gcaagaggca aatgaaatag   2580
attgacctcc caataacacc acgtagttat tgggaggtca atctatgaaa tgcgattaag   2640
```

```
ggccggccga agcaaactta agagtgtgtt gatagtgcag tatcttaaaa ttttgtataa    2700
taggaattga agttaaatta gatgctaaaa atttgtaatt aagaaggagt gattacatga    2760
acaaaaatat aaaatattct caaaactttt taacgagtga aaaagtactc aaccaaataa    2820
taaaacaatt gaatttaaaa gaaaccgata ccgtttacga aattggaaca ggtaaagggc    2880
atttaacgac gaaactggct aaaataagta acaggtaac gtctattgaa ttagacagtc    2940
atctattcaa cttatcgtca gaaaaattaa aactgaatac tcgtgtcact ttaattcacc    3000
aagatattct acagtttcaa ttccctaaca acagaggta taaaattgtt gggagtattc    3060
cttaccattt aagcacacaa attattaaaa agtggtttt tgaaagccat gcgtctgaca    3120
tctatctgat tgttgaagaa ggattctaca agcgtacctt ggatattcac cgaacactag    3180
ggttgctctt gcacactcaa gtctcgattc agcaattgct taagctgcca gcggaatgct    3240
ttcatcctaa accaaaagta acagtgtct taataaaact tacccgccat accacagatg    3300
ttccagataa atattggaag ctatatacgt actttgtttc aaaatgggtc aatcgagaat    3360
atcgtcaact gtttactaaa aatcagtttc atcaagcaat gaaacacgcc aaagtaaaca    3420
atttaagtac cgttacttat gagcaagtat tgtctatttt taatagttat ctattattta    3480
acgggaggaa ataattctat gagtcgcttt tgtaaatttg gaaagttaca cgttactaaa    3540
gggaatgtgt tt    3552

<210> SEQ ID NO 4
<211> LENGTH: 4299
<212> TYPE: DNA
<213> ORGANISM: Artificial Sequence
<220> FEATURE:
<223> OTHER INFORMATION: plasmid pMTL 83245

<400> SEQUENCE: 4
aaactccttt ttgataatct catgaccaaa atcccttaac gtgagttttc gttccactga      60
gcgtcagacc ccgtagaaaa gatcaaagga tcttcttgag atcctttttt tctgcgcgta     120
atctgctgct tgcaaacaaa aaaccaccg ctaccagcgg tggtttgttt gccggatcaa     180
gagctaccaa ctcttttcc gaaggtaact ggcttcagca gagcgcagat accaaatact     240
gttcttctag tgtagccgta gttaggccac cacttcaaga actctgtagc accgcctaca     300
tacctcgctc tgctaatcct gttaccagtg gctgctgcca gtggcgataa gtcgtgtctt     360
accgggttgg actcaagacg atagttaccg gataaggcgc agcggtcggg ctgaacgggg     420
ggttcgtgca cacagcccag cttggagcga acgacctaca ccgaactgag atacctacag     480
cgtgagctat gagaaagcgc cacgcttccc gaagggagaa aggcggacag gtatccggta     540
agcggcaggg tcggaacagg agagcgcacg agggagcttc caggggggaaa cgcctggtat     600 ctttatagtc ctgtcgggtt tcgccacctc tgacttgagc gtcgatttt gtgatgctcg     660 tcagggggc ggagcctatg gaaaaacgcc agcaacgcgg cctttttacg gttcctggcc     720
ttttgctggc cttttgctca catgttcttt cctgcgttat cccctgattc tgtggataac     780
cgtattaccg cctttgagtg agctgatacc gctcgccgca gccgaacgac cgagcgcagc     840
gagtcagtga gcgaggaagc ggaagagcgc ccaatacgca gggccccctg caggataaaa     900
aaattgtaga taaattttat aaaatagttt tatctacaat ttttttatca ggaaacagct     960
atgaccgcgg ccgcaatatg atatttatgt ccattgtgaa agggattata ttcaactatt    1020
attccagtta cgttcataga aatttttcctt tctaaaatat tttattccat gtcaagaact    1080
```

```
ctgtttattt cattaaagaa ctataagtac aaagtataag gcatttgaaa aaataggcta    1140
gtatattgat tgattattta ttttaaaatg cctaagtgaa atatatacat attataacaa    1200
taaaataagt attagtgtag gattttttaaa tagagtatct attttcagat taaattttg    1260 attatttgat ttacattata taatattgag taaagtattg actagcaaaa ttttttgata    1320
ctttaatttg tgaaatttct tatcaaaagt tatattttg aataattttt attgaaaaat    1380
acaactaaaa aggattatag tataagtgtg tgtaattttg tgttaaattt aaagggagga    1440
aatgaacatg aaacatatgg tgaccatgat tacgaattcg agctcggtac ccggggatcc    1500
tctagagtcg acgtcacgcg tccatggaga tctcgaggcc tgcagacatg caagcttggc    1560
actggccgtc gttttacaac gtcgtgactg ggaaaaccct ggcgttaccc aacttaatcg    1620
ccttgcagca catccccctt cgccagctg gcgtaatagc gaagaggccc gcaccgatcg    1680
cccttcccaa cagttgcgca gcctgaatgg cgaatggcgc tagcataaaa ataagaagcc    1740
tgcatttgca ggcttcttat ttttatggcg cgccgccatt attttttga acaattgaca    1800 attcatttct tattttttat taagtgatag tcaaaaggca taacagtgct gaatagaaag    1860
aaatttacag aaaagaaaat tatagaattt agtatgatta attatactca tttatgaatg    1920
tttaattgaa tacaaaaaaa aatacttgtt atgtattcaa ttacgggtta aaatatagac    1980
aagttgaaaa atttaataaa aaaataagtc ctcagctctt atatattaag ctaccaactt    2040
agtatataag ccaaaactta aatgtgctac caacacatca agccgttaga gaactctatc    2100
tatagcaata tttcaaatgt accgacatac aagagaaaca ttaactatat atattcaatt    2160
tatgagatta tcttaacaga tataaatgta aattgcaata agtaagattt agaagtttat    2220
agcctttgtg tattggaagc agtacgcaaa ggcttttta tttgataaaa attagaagta    2280
tatttatttt ttcataatta atttatgaaa atgaaagggg gtgagcaaag tgacagagga    2340
aagcagtatc ttatcaaata acaaggtatt agcaatatca ttattgactt tagcagtaaa    2400
cattatgact tttatagtgc ttgtagctaa gtagtacgaa agggggagct ttaaaaagct    2460
ccttggaata catagaattc ataaattaat ttatgaaaag aagggcgtat atgaaaactt    2520
gtaaaaattg caaagagttt attaaagata ctgaaatatg caaaatacat tcgttgatga    2580
ttcatgataa aacagtagca acctattgca gtaaatacaa tgagtcaaga tgtttacata    2640
aagggaaagt ccaatgtatt aattgttcaa agatgaaccg atatggatgg tgtgccataa    2700
aaatgagatg ttttacagag gaagaacaga aaaagaacg tacatgcatt aaatattatg    2760
caaggagctt taaaaagct catgtaaaga agagtaaaaa gaaaaaataa tttatttatt    2820
aatttaatat tgagagtgcc gacacagtat gcactaaaaa atatatctgt ggtgtagtga    2880
gccgatacaa aaggatagtc actcgcatt tcataataca tcttatgtta tgattatgtg    2940
tcggtgggac ttcacgacga aaacccacaa taaaaaaaga gttcggggta gggttaagca    3000
tagttgaggc aactaaacaa tcaagctagg atatgcagta gcagaccgta aggtcgttgt    3060
ttaggtgtgt tgtaatacat acgctattaa gatgtaaaaa tacggatacc aatgaaggga    3120
aaagtataat ttttggatgt agtttgtttg ttcatctatg ggcaaactac gtccaaagcc    3180
gtttccaaat ctgctaaaaa gtatatcctt tctaaaatca agtcaagta tgaaatcata    3240 aataaagttt aattttgaag ttattatgat attatgtttt tctattaaaa taaattaagt    3300
atatagaata gtttaataat agtatatact taatgtgata agtgtctgac agtgtcacag    3360
aaaggatgat tgttatggat tataagcggc cggccgaagc aaacttaaga gtgtgttgat    3420
agtgcagtat cttaaaattt tgtataatag gaattgaagt taaattagat gctaaaaatt    3480
```

```
tgtaattaag aaggagtgat tacatgaaca aaaatataaa atattctcaa aactttttaa    3540
cgagtgaaaa agtactcaac caaataataa aacaattgaa tttaaaagaa accgataccg    3600
tttacgaaat tggaacaggt aaagggcatt taacgacgaa actggctaaa ataagtaaac    3660
aggtaacgtc tattgaatta gacagtcatc tattcaactt atcgtcagaa aaattaaaac    3720
tgaatactcg tgtcacttta attccaccaag atattctaca gtttcaattc cctaacaaac    3780
agaggtataa aattgttggg agtattcctt accatttaag cacacaaatt attaaaaaag    3840
tggtttttga aagccatgcg tctgacatct atctgattgt tgaagaagga ttctacaagc    3900
gtaccttgga tattcaccga acactagggt tgctcttgca cactcaagtc tcgattcagc    3960
aattgcttaa gctgccagcg gaatgctttc atcctaaacc aaaagtaaac agtgtcttaa    4020
taaaacttac ccgccatacc acagatgttc cagataaata ttggaagcta tacgtact     4080 ttgtttcaaa atgggtcaat cgagaatatc gtcaactgtt tactaaaaat cagtttcatc    4140
aagcaatgaa acacgccaaa gtaaacaatt taagtaccgt tacttatgag caagtattgt    4200
ctatttttaa tagttatcta ttatttaacg ggaggaaata attctatgag tcgcttttgt    4260
aaatttggaa agttacacgt tactaaaggg aatgtgttt                          4299

<210> SEQ ID NO 5
<211> LENGTH: 7884
<212> TYPE: DNA
<213> ORGANISM: Artificial Sequence
<220> FEATURE:
<223> OTHER INFORMATION: plasmid pMTL83245-SDR

<400> SEQUENCE: 5
aaactccttt ttgataatct catgaccaaa atcccttaac gtgagttttc gttccactga      60
gcgtcagacc ccgtagaaaa gatcaaagga tcttcttgag atcctttttt tctgcgcgta     120
atctgctgct tgcaaacaaa aaaccaccg ctaccagcgg tggtttgttt gccggatcaa     180
gagctaccaa ctcttttccc gaaggtaact ggcttcagca gagcgcagat accaaatact     240
gttcttctag tgtagccgta gttaggccac cacttcaaga actctgtagc accgcctaca     300
tacctcgctc tgctaatcct gttaccagtg gctgctgcca gtggcgataa gtcgtgtctt     360
accgggttgg actcaagacg atagttaccg gataaggcgc agcggtcggg ctgaacgggg     420
ggttcgtgca cacagcccag cttggagcga acgacctaca ccgaactgag atacctacag     480
cgtgagctat gagaaagcgc cacgcttccc gaagggagaa aggcggacag gtatccggta     540
agcggcaggg tcggaacagg agagcgcacg agggagcttc cagggggaaa cgcctggtat     600
ctttatagtc ctgtcgggtt tcgccacctc tgacttgagc gtcgatttt gtgatgctcg     660 tcagggggg ggagcctatg gaaaaacgcc agcaacgcgg cctttttacg gttcctggcc     720
ttttgctggc cttttgctca catgttcttt cctgcgttat cccctgattc tgtggataac     780
cgtattaccg cctttgagtg agctgatacc gctcgccgca gccgaacgac cgagcgcagc     840
gagtcagtga gcgaggaagc ggaagagcgc ccaatacgca gggccccctg caggataaaa     900
aaattgtaga taaattttat aaaatagttt tatctacaat tttttatca ggaaacagct      960 atgaccgcgg ccgcaatatg atatttatgt ccattgtgaa agggattata ttcaactatt    1020
attccagtta cgtccataga aattttcctt tctaaaatat tttattccat gtcaagaact    1080
ctgtttattt cattaaagaa ctataagtac aaagtataag gcatttgaaa aaataggcta    1140
gtatattgat tgattattta ttttaaaatg cctaagtgaa atatatacat attataacaa    1200
```

```
taaaataagt attagtgtag gattttttaaa tagagtatct attttcagat taaattttttg      1260
attatttgat ttacattata taatattgag taaagtattg actagcaaaa ttttttgata      1320
ctttaatttg tgaaatttct tatcaaaagt tatattttttg aataatttttt attgaaaaat      1380
acaactaaaa aggattatag tataagtgtg tgtaatttttg tgttaaatttt aaagggagga      1440
aatgaacatg aaacatatgt caggaacagg tagattagct ggaaaaattg cattaattac      1500
aggtggtgct ggtaatatag gatcagaatt aactagaaga tttcttgctg aaggtgcaac      1560
tgttattata tcaggtagaa atagagcaaa acttactgca ttagcagaga gaatgcaagc      1620
agaagcaggt gttccagcaa aaagaattga tcttgaagta atggatggtt cagatcctgt      1680
tgcagttaga gctggaatag aagctattgt tgctagacat ggacagatag atatattagt      1740
taataatgct ggaagtgctg gtgcacagag aagattagct gaaattccac ttactgaagc      1800
agaattagga ccaggtgcag aagagactct tcatgcttct atagctaatt tattaggtat      1860
gggttggcat ttaatgagaa tagctgcacc acacatgcct gttggaagtg cagtaataaa      1920
tgtttcaact atatttttcaa gagctgaata ttatggtaga ataccttacg taacacctaa      1980
agctgcactt aatgcacttt ctcaattagc agcaagagaa cttggtgcta gaggtataag      2040
agtaaacaca atatttcctg gaccaataga gtcagataga attagaacag tatttcagag      2100
aatggatcaa cttaaaggaa gacctgaagg tgatacagct catcatttttc ttaatactat      2160
gagactttgt agagcaaatg atcaaggtgc attagagaga agatttccaa gtgttggtga      2220
tgtagcagac gctgctgtat ttttagctag tgctgaatca gcagcattat caggtgaaac      2280
aattgaagta actcatggta tggaattacc agcttgttca gagacttctt tattagcaag      2340
aactgactta agaactatag atgcttcagg tagaacaact cttatatgtg ctggtgatca      2400
aattgaagaa gtaatggctt taacaggaat gttaagaact tgcggatctg aagtaattat      2460
aggatttaga tcagctgcag cattagcaca gtttgagcag gcagtaaatg aatctagaag      2520
acttgcaggt gcagatttca ctccacctat agcattacca cttgacccaa gagatccagc      2580
tactatagat gctgtatttg attgggctgg tgaaaataca ggtggtatac atgcagcagt      2640
aatattacct gcaactagtc atgaaccagc accatgtgtt attgaagttg atgatgagag      2700
agtacttaac ttttttagctg atgaaataac aggaacaatt gtaatagcaa gtagacttgc      2760
aagatattgg caatctcaga gacttacacc aggtgctaga gcaagaggtc caagagtaat      2820
ttttcttagt aatggtgctg atcagaatgg aaatgtatat ggtagaatac agtcagctgc      2880
aattggacaa ttaataagag tttggagaca tgaggctgaa cttgattatc aaagagcttc      2940
agcagctggt gaccatgttc ttccacctgt atgggcaaat cagattgtaa gatttgctaa      3000
tagaagtctt gaaggtcttg aatttgcttg tgcttggact gctcaacttt tacattctca      3060
aagacacata aatgaaataa ctttaaatat accagcaaac attagtgcaa ctacaggtgc      3120
aagatcagct agtgttggtt gggctgaatc tttaattgga cttcatttag gaaaggtagc      3180
tcttataaca ggtggttcag ctggaatagg tggtcaaata ggaagacttt tagcacttag      3240
tggtgctaga gtaatgcttg ctgcaagaga tagacacaaa ttagaacaaa tgcaagcaat      3300
gattcagagt gaacttgcag aagttggata tactgatgtt gaagacagag ttcatatagc      3360
tcctggatgt gatgtaagtt ctgaagctca gttagcagat cttgttgaga gaactttatc      3420
tgcattcgga acagttgatt atcttataaa taatgcaggt atagcaggtg ttgaagaaat      3480
ggttatagat atgcctgtag aaggttggag acatacactt tttgctaacc ttatatcaaa      3540
ctattcttta atgagaaaat tagctccact tatgaaaaag caaggaagtg gttatatact      3600
```

```
taatgtatca tcatatttcg gtggtgaaaa agatgcagct ataccatacc caaatagagc    3660
agattatgct gtaagtaaag caggacagag agctatggct gaagtatttg ctagattctt    3720
aggaccagaa attcagatta atgctatagc accaggacca gtagaaggtg acagacttag    3780
aggtactggt gaaagacctg gacttttttgc tagaagagct agattaatac ttgaaaataa    3840
gagacttaat gagcttcatg ctgctttaat agctgctgct agaacagatg agagatcaat    3900
gcatgaactt gtagaacttt tattaccaaa tgacgtagca gcattagagc aaaacccagc    3960
agctcctaca gctcttagag aacttgctag aagatttaga tcagaaggtg atcctgctgc    4020
aagttcttct agtgcacttt taaatagaag tatagctgca aaacttttag caagattaca    4080
taacggtggt tatgtattac ctgctgatat attcgcaaat ttaccaaacc ctccagatcc    4140
tttctttact agagcacaaa tagacagaga agcaagaaaa gtaagagatg aattatggg    4200 aatgctttat ttacaaagaa tgccaactga gtttgacgtt gcaatggcta ctgtatatta    4260
tttagcagat agaaatgttt ctggtgaaac ttttcatcca tcaggtggtt taagatacga    4320
aagaacacct acaggtggtg aattattcgg acttccttct ccagaaagac ttgcagaatt    4380
agtaggatca acagtttatc ttataggtga acatttaact gagcacctta atttacttgc    4440
tagagcatat cttgaaagat atggtgcaag acaagtagtt atgatagtag agacagagac    4500
tggtgcagaa acaatgagaa gattacttca tgatacgtt gaagctggta gattaatgac    4560
tattgtagca ggtgatcaga tagaagctgc tattgatcaa gctattacaa gatatggtag    4620
accaggacct gttgtatgta ctcctttag acctcttcct actgttccat tagtaggtag    4680
aaaggattct gactggtcaa cagttttaag tgaagcagaa tttgctgagt tatgcgaaca    4740
tcaattaaca catcactta gagttgctag aaagatagct ttatcagatg gtgcatcttt    4800
agcattagta actccagaga ctactgcaac tagtacaact gaacaattcg cattagctaa    4860
ttttataaag acaacattac acgctttac tgctacaatt ggtgtagaaa gtgaaagaac    4920
tgcacaaaga attttaatta accaggttga tttaacaaga agagcaagag ctgaagaacc    4980
tagagatcct catgagagac aacaagagct gaaagatt atagaagctg ttcttcttgt    5040
tacagcacct ttacctccag aagcagatac tagatacgca ggtagaatac atagaggtag    5100
agcaataaca gtataactcg aggcctgcag acatgcaagc ttggcactgg ccgtcgtttt    5160
acaacgtcgt gactgggaaa accctggcgt tacccaactt aatcgccttg cagcacatcc    5220
ccctttcgcc agctggcgta atagcgaaga ggcccgcacc gatcgccctt cccaacagtt    5280
gcgcagcctg aatggcgaat ggcgctagca taaaataag aagcctgcat ttgcaggctt    5340 cttatttta tggcgcgccg ccattatttt tttgaacaat tgacaattca tttcttattt    5400
tttattaagt gatagtcaaa aggcataaca gtgctgaata gaaagaaatt tacagaaaag    5460
aaaattatag aatttagtat gattaattat actcatttat gaatgtttaa ttgaatacaa    5520
aaaaaaatac ttgttatgta ttcaattacg ggttaaaata tagacaagtt gaaaaattta    5580 ataaaaaat aagtcctcag ctcttatata ttaagctacc aacttagtat ataagccaaa    5640
acttaaatgt gctaccaaca catcaagccg ttagagaact ctatctatag caatatttca    5700
aatgtaccga catacaagag aaacattaac tatatatatt caatttatga gattatctta    5760
acagatataa atgtaaattg caataagtaa gatttagaag tttatagcct ttgtgtattg    5820
gaagcagtac gcaaaggctt ttttatttga taaaaattag aagtatattt atttttttcat    5880 aattaattta tgaaaatgaa aggggggtgag caaagtgaca gaggaaagca gtatcttatc    5940
```

| | | | | |
|---|---|---|---|---|
| aaataacaag | gtattagcaa | tatcattatt | gactttagca | gtaaacatta tgactttat | 6000 |
| agtgcttgta | gctaagtagt | acgaaagggg | gagctttaaa | aagctccttg gaatacatag | 6060 |
| aattcataaa | ttaatttatg | aaagaaggg | cgtatatgaa | aacttgtaaa aattgcaaag | 6120 |
| agttttattaa | agatactgaa | atatgcaaaa | tacattcgtt | gatgattcat gataaaacag | 6180 |
| tagcaaccta | ttgcagtaaa | tacaatgagt | caagatgttt | acataaaggg aaagtccaat | 6240 |
| gtattaattg | ttcaaagatg | aaccgatatg | gatggtgtgc | cataaaaatg agatgtttta | 6300 |
| cagaggaaga | acagaaaaaa | gaacgtacat | gcattaaata | ttatgcaagg agctttaaaa | 6360 |
| aagctcatgt | aaagaagagt | aaaaagaaaa | aataatttat | ttattaatttt aatattgaga | 6420 |
| gtgccgacac | agtatgcact | aaaaaatata | tctgtggtgt | agtgagccga tacaaaagga | 6480 |
| tagtcactcg | cattttcata | atacatctta | tgttatgatt | atgtgtcggt gggacttcac | 6540 |
| gacgaaaacc | cacaataaaa | aaagagttcg | gggtaggggtt | aagcatagtt gaggcaacta | 6600 |
| aacaatcaag | ctaggatatg | cagtagcaga | ccgtaaggtc | gttgtttagg tgtgttgtaa | 6660 |
| tacatacgct | attaagatgt | aaaaatacgg | ataccaatga | agggaaaagt ataattttg | 6720 |
| gatgtagttt | gtttgttcat | ctatgggcaa | actacgtcca | agccgttttc caaatctgct | 6780 |
| aaaaagtata | tcctttctaa | aatcaaagtc | aagtatgaaa | tcataaataa agtttaattt | 6840 |
| tgaagttatt | atgatattat | gttttctat | taaaataaat | taagtatata gaatagttta | 6900 |
| ataatagtat | atacttaatg | tgataagtgt | ctgacagtgt | cacagaaagg atgattgtta | 6960 |
| tggattataa | gcggccggcc | gaagcaaact | taagagtgtg | ttgatagtgc agtatcttaa | 7020 |
| aattttgtat | aataggaatt | gaagttaaat | tagatgctaa | aaattttgtaa ttaagaagga | 7080 |
| gtgattacat | gaacaaaaat | ataaaatatt | ctcaaaactt | tttaacgagt gaaaagtac | 7140 |
| tcaaccaaat | aataaaacaa | ttgaatttaa | agaaaccga | taccgtttac gaaattggaa | 7200 |
| caggtaaagg | gcatttaacg | acgaaactgg | ctaaaataag | taaacaggta acgtctattg | 7260 |
| aattagacag | tcatctattc | aacttatcgt | cagaaaaatt | aaaactgaat actcgtgtca | 7320 |
| ctttaattca | ccaagatatt | ctacagtttc | aattccctaa | caaacagagg tataaaattg | 7380 |
| ttgggagtat | tccttaccat | ttaagcacac | aaattattaa | aaaagtggtt tttgaaagcc | 7440 |
| atgcgtctga | catctatctg | attgttgaag | aaggattcta | caagcgtacc ttggatattc | 7500 |
| accgaacact | agggttgctc | ttgcacactc | aagtctcgat | tcagcaattg cttaagctgc | 7560 |
| cagcggaatg | ctttcatcct | aaaccaaaag | taaacagtgt | cttaataaaa cttacccgcc | 7620 |
| ataccacaga | tgttccagat | aaatattgga | agctatatac | gtactttgtt tcaaaatggg | 7680 |
| tcaatcgaga | atatcgtcaa | ctgtttacta | aaaatcagtt | tcatcaagca atgaaacacg | 7740 |
| ccaaagtaaa | caatttaagt | accgttactt | atgagcaagt | attgtctatt tttaatagtt | 7800 |
| atctattatt | taacgggagg | aaataattct | atgagtcgct | tttgtaaatt tggaaagtta | 7860 |
| cacgttacta | aagggaatgt | gttt | | | 7884 |

<210> SEQ ID NO 6
<211> LENGTH: 601
<212> TYPE: PRT
<213> ORGANISM: Artificial Sequence
<220> FEATURE:
<223> OTHER INFORMATION: Type II methyltransferase

<400> SEQUENCE: 6

Met Phe Pro Cys Asn Ala Tyr Ile Glu Tyr Gly Asp Lys Asn Met Asn
1               5                   10                  15

```
Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Tyr Lys Gln Lys
        35                  40                  45

Ser Asn Met Lys Lys Glu Ile Ser Phe Ser Glu Glu Tyr Tyr Lys Gln
 50                  55                  60

Lys Ile Met Asn Gly Lys Asn Gly Val Val Tyr Thr Pro Pro Glu Met
 65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140

Ser Tyr His Ile Val Arg Asn Asn Leu Phe Gly Phe Asp Ile Asp Glu
145                 150                 155                 160

Thr Ala Ile Lys Val Leu Lys Ile Asp Leu Phe Leu Ile Ser Asn Gln
                165                 170                 175

Phe Ser Glu Lys Asn Phe Gln Val Lys Asp Phe Leu Val Glu Asn Ile
            180                 185                 190

Asp Arg Lys Tyr Asp Val Phe Ile Gly Asn Pro Pro Tyr Ile Gly His
        195                 200                 205

Lys Ser Val Asp Ser Ser Tyr Ser Tyr Val Leu Arg Lys Ile Tyr Gly
    210                 215                 220

Ser Ile Tyr Arg Asp Lys Gly Asp Ile Ser Tyr Cys Phe Phe Gln Lys
225                 230                 235                 240

Ser Leu Lys Cys Leu Lys Glu Gly Gly Lys Leu Val Phe Val Thr Ser
                245                 250                 255

Arg Tyr Phe Cys Glu Ser Cys Ser Gly Lys Glu Leu Arg Lys Phe Leu
            260                 265                 270

Ile Glu Asn Thr Ser Ile Tyr Lys Ile Ile Asp Phe Tyr Gly Ile Arg
        275                 280                 285

Pro Phe Lys Arg Val Gly Ile Asp Pro Met Ile Ile Phe Leu Val Arg
    290                 295                 300

Thr Lys Asn Trp Asn Asn Asn Ile Glu Ile Ile Arg Pro Asn Lys Ile
305                 310                 315                 320

Glu Lys Asn Glu Lys Asn Lys Phe Leu Asp Ser Leu Phe Leu Asp Lys
                325                 330                 335

Ser Glu Lys Cys Lys Lys Phe Ser Ile Ser Gln Lys Ser Ile Asn Asn
            340                 345                 350

Asp Gly Trp Val Phe Val Asp Glu Val Glu Lys Asn Ile Ile Asp Lys
        355                 360                 365

Ile Lys Glu Lys Ser Lys Phe Ile Leu Lys Asp Ile Cys His Ser Cys
    370                 375                 380

Gln Gly Ile Ile Thr Gly Cys Asp Arg Ala Phe Ile Val Asp Arg Asp
385                 390                 395                 400

Ile Ile Asn Ser Arg Lys Ile Glu Leu Arg Leu Ile Lys Pro Trp Ile
                405                 410                 415

Lys Ser Ser His Ile Arg Lys Asn Glu Val Ile Lys Gly Glu Lys Phe
            420                 425                 430

Ile Ile Tyr Ser Asn Leu Ile Glu Asn Glu Thr Glu Cys Pro Asn Ala
```

Ile Lys Tyr Ile Glu Gln Tyr Lys Lys Arg Leu Met Glu Arg Glu
450                 455                 460

Cys Lys Lys Gly Thr Arg Lys Trp Tyr Glu Leu Gln Trp Gly Arg Lys
465                 470                 475                 480

Pro Glu Ile Phe Glu Lys Lys Ile Val Phe Pro Tyr Lys Ser Cys
                485                 490                 495

Asp Asn Arg Phe Ala Leu Asp Lys Gly Ser Tyr Phe Ser Ala Asp Ile
            500                 505                 510

Tyr Ser Leu Val Leu Lys Lys Asn Val Pro Phe Thr Tyr Glu Ile Leu
        515                 520                 525

Leu Asn Ile Leu Asn Ser Pro Leu Tyr Glu Phe Tyr Phe Lys Thr Phe
    530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
                565                 570                 575

Glu Lys Lys Leu Tyr Asp Phe Phe Gly Leu Thr Asp Lys Glu Ile Glu
            580                 585                 590

Ile Val Glu Lys Ile Lys Asp Asn Cys
        595                 600

<210> SEQ ID NO 7
<211> LENGTH: 4709
<212> TYPE: DNA
<213> ORGANISM: Artificial Sequence
<220> FEATURE:
<223> OTHER INFORMATION: designed methylation plasmid

<400> SEQUENCE: 7
gtttgccacc tgacgtctaa gaaaggaat attcagcaat tgcccgtgc cgaagaaagg      60
cccacccgtg aaggtgagcc agtgagttga ttgctacgta attagttagt tagcccttag    120
tgactcgtaa tacgactcac tatagggctc gaggcggccg cgcaacgcaa ttaatgtgag    180
ttagctcact cattaggcac cccaggcttt acactttatg cttccggctc gtatgttgtg    240
tggaattgtg agcggataac aatttcacac aggaaacaca tatgtttccg tgcaatgcct    300
atatcgaata tggtgataaa aatatgaaca gctttatcga agatgtggaa cagatctaca    360
acttcattaa aagaacatt gatgtggaag aaaagatgca tttcattgaa acctataaac    420
agaaaagcaa catgaagaaa gagattagct ttagcgaaga atactataaa cagaagatta    480
tgaacggcaa aaatggcgtt gtgtacaccc cgccggaaat ggcggccttt atggttaaaa    540
atctgatcaa cgttaacgat gttattggca atccgtttat taaatcatt gacccgagct    600
gcggtagcgg caatctgatt tgcaaatgtt ttctgtatct gatcgcatc tttattaaga    660
acattgaggt gattaacagc aaaaataacc tgaatctgaa actggaagac atcagctacc    720
acatcgttcg caacaatctg tttggcttcg atattgacga accgcgatc aaagtgctga    780
aaattgatct gtttctgatc agcaaccaat ttagcgagaa aaatttccag gttaaagact    840
ttctggtgga aaatattgat cgcaaatatg acgtgttcat ggtaatccg ccgtatatcg    900
gtcacaaaag cgtggacagc agctacagct acgtgctgcg caaaatctac ggcagcatct    960
accgcgacaa aggcgatatc agctattgtt tctttcagaa gagcctgaaa tgtctgaagg   1020
aaggtggcaa actggtgttt gtgaccagcc gctacttctg cgagagctgc agcggtaaag   1080
aactgcgtaa attcctgatc gaaaacacga gcatttacaa gatcattgat ttttacggca   1140

```
tccgcccgtt caaacgcgtg ggtatcgatc cgatgattat tttctggtt cgtacgaaga   1200 actggaacaa taacattgaa attattcgcc cgaacaagat tgaaaagaac gaaaagaaca   1260
aattcctgga tagcctgttc ctggacaaaa gcgaaaagtg taaaaagttt agcattagcc   1320
agaaaagcat taataacgat ggctgggttt cgtggacga agtggagaaa acattatcg    1380 acaaaatcaa agagaaaagc aagttcattc tgaaagatat ttgccatagc tgtcaaggca   1440
ttatcaccgg ttgtgatcgc gcctttattg tggaccgtga tatcatcaat agccgtaaga   1500
tcgaactgcg tctgattaaa ccgtggatta aaagcagcca tatccgtaag aatgaagtta   1560
ttaagggcga aaaattcatc atctatagca acctgattga aatgaaaccc gagtgtccga   1620
atgcgattaa atatatcgaa cagtacaaga acgtctgat ggagcgccgc gaatgcaaaa    1680
agggcacgcg taagtggtat gaactgcaat ggggccgtaa accggaaatc ttcgaagaaa   1740
agaaaattgt tttcccgtat aaaagctgtg acaatcgttt tgcactggat aagggtagct   1800
attttagcgc agacatttat agcctggttc tgaagaaaaa tgtgccgttc acctatgaga   1860
tcctgctgaa tatcctgaat agcccgctgt acgagtttta ctttaagacc ttcgcgaaaa   1920
agctgggcga gaatctgtac gagtactatc cgaacaacct gatgaagctg tgcatcccga   1980
gcatcgattt cggcggtgag aacaatattg agaaaaagct gtatgatttc tttggtctga   2040
cggataaaga aattgagatt gtggagaaga tcaaagataa ctgctaagaa ttcgatatca   2100
cccgggaact agtctgcagc cctttagtga gggttaattg gagtcactaa gggttagtta   2160
gttagattag cagaaagtca aaagcctccg accggaggct tttgactaaa acttcccttg   2220
gggttatcat tggggctcac tcaaaggcgg taatcagata aaaaaaatcc ttagctttcg   2280
ctaaggatga tttctgctag agatggaata gactggatgg aggcggataa agttgcagga   2340
ccacttctgc gctcggccct tccggctggc tggtttattg ctgataaatc tggagccggt   2400
gagcgtgggt ctcgcggtat cattgcagca ctggggccag atggtaagcc ctcccgtatc   2460
gtagttatct acacgacggg gagtcaggca actatggatg aacgaaatag acagatcgct   2520
gagataggtg cctcactgat taagcattgg taactgtcag accaagttta ctcatatata   2580
ctttagattg atttaaaact tcattttaa tttaaaagga tctaggtgaa gatccttttt    2640
gataatctca tgaccaaaat cccttaacgt gagttttcgt tccactgagc gtcagacccc   2700
ttaataagat gatcttcttg agatcgtttt ggtctgcgcg taatctcttg ctctgaaaac   2760 gaaaaaccg ccttgcaggg cggttttttcg aaggttctct gagctaccaa ctctttgaac   2820
cgaggtaact ggcttggagg agcgcagtca ccaaaacttg tcctttcagt ttagccttaa   2880
ccggcgcatg acttcaagac taactcctct aaatcaatta ccagtggctg ctgccagtgg   2940
tgcttttgca tgtctttccg ggttggactc aagacgatag ttaccggata aggcgcagcg   3000
gtcggactga acgggggttt cgtgcataca gtccagcttg gagcgaactg cctacccgga   3060
actgagtgtc aggcgtggaa tgagacaaac gcggccataa cagcggaatg acaccggtaa   3120
accgaaaggc aggaacagga gagcgcacga gggagccgcc aggggaaacg cctggtatct   3180
ttatagtcct gtcgggtttc gccaccactg atttgagcgt cagatttcgt gatgcttgtc   3240
aggggggcgg agcctatgga aaacggcttt gccgcggcc ctctcacttc cctgttaagt    3300
atcttcctgg catcttccag gaaatctccg ccccgttcgt aagccatttc cgctcgccgc   3360
agtcgaacga ccgagcgtag cgagtcagtg agcgaggaag cggaatatat cctgtatcac   3420
atattctgct gacgcaccgg tgcagccttt tttctcctgc cacatgaagc acttcactga   3480
```

```
cacccctcatc agtgccaaca tagtaagcca gtatacactc cgctagcgct gaggtctgcc    3540
tcgtgaagaa ggtgttgctg actcatacca ggcctgaatc gccccatcat ccagccagaa    3600
agtgagggag ccacggttga tgagagcttt gttgtaggtg gaccagttgg tgattttgaa    3660
cttttgcttt gccacggaac ggtctgcgtt gtcgggaaga tgcgtgatct gatccttcaa    3720
ctcagcaaaa gttcgattta ttcaacaaag ccacgttgtg tctcaaaatc tctgatgtta    3780
cattgcacaa gataaaaata tatcatcatg aacaataaaa ctgtctgctt acataaacag    3840
taatacaagg ggtgtttact agaggttgat cgggcacgta agaggttcca actttcacca    3900
taatgaaata agatcactac cgggcgtatt ttttgagtta tcgagatttt caggagctaa    3960
ggaagctaaa atggagaaaa aaatcacggg atataccacc gttgatatat cccaatggca    4020
tcgtaaagaa cattttgagg catttcagtc agttgctcaa tgtacctata accagaccgt    4080
tcagctggat attacggcct ttttaaagac cgtaaagaaa aataagcaca gtttttatcc    4140
ggcctttatt cacattcttg cccgcctgat gaacgctcac ccggagtttc gtatggccat    4200
gaaagacggt gagctggtga tctgggatag tgttcaccct tgttacaccg ttttccatga    4260
gcaaactgaa acgttttcgt ccctctggag tgaataccac gacgatttcc ggcagtttct    4320
ccacatatat tcgcaagatg tggcgtgtta cggtgaaaac ctggcctatt tccctaaagg    4380
gtttattgag aatatgtttt ttgtctcagc caatccctgg gtgagtttca ccagttttga    4440
tttaaacgtg gccaatatgg acaacttctt cgcccccgtt ttcacgatgg caaatatta    4500 tacgcaaggc gacaaggtgc tgatgccgct ggcgatccag gttcatcatg ccgtttgtga    4560
tggcttccat gtcggccgca tgcttaatga attacaacag tactgtgatg agtggcaggg    4620
cggggcgtaa taatactagc tccggcaaaa aaacgggcaa ggtgtcacca ccctgccctt    4680
tttctttaaa accgaaaaga ttacttcgc                                      4709

<210> SEQ ID NO 8
<211> LENGTH: 28
<212> TYPE: DNA
<213> ORGANISM: Artificial Sequence
<220> FEATURE:
<223> OTHER INFORMATION: oligonucleotide Ppta-ack-NotI-F

<400> SEQUENCE: 8
gagcggccgc aatatgatat ttatgtcc                                        28

<210> SEQ ID NO 9
<211> LENGTH: 28
<212> TYPE: DNA
<213> ORGANISM: Artificial Sequence
<220> FEATURE:
<223> OTHER INFORMATION: oligonucleotide Ppta-ack-NdeI-R

<400> SEQUENCE: 9
ttccatatgt ttcatgttca tttcctcc                                        28

<210> SEQ ID NO 10
<211> LENGTH: 17
<212> TYPE: DNA
<213> ORGANISM: Artificial Sequence
<220> FEATURE:
<223> OTHER INFORMATION: oligonucleotide M13R

<400> SEQUENCE: 10
caggaaacag ctatgac                                                    17
```

```
<210> SEQ ID NO 11
<211> LENGTH: 24
<212> TYPE: DNA
<213> ORGANISM: Artificial Sequence
<220> FEATURE:
<223> OTHER INFORMATION: oligonucleotide SDR_seqR1

<400> SEQUENCE: 11
agcagcttct atctgatcac ctgc                                          24

<210> SEQ ID NO 12
<211> LENGTH: 25
<212> TYPE: DNA
<213> ORGANISM: Artificial Sequence
<220> FEATURE:
<223> OTHER INFORMATION: oligonucleotide SDR_seqR2

<400> SEQUENCE: 12
tgctctaatg ctgctacgtc atttg                                         25

<210> SEQ ID NO 13
<211> LENGTH: 24
<212> TYPE: DNA
<213> ORGANISM: Artificial Sequence
<220> FEATURE:
<223> OTHER INFORMATION: oligonucleotide SDR_seqR3

<400> SEQUENCE: 13
tgcaagttca ctctgaatca ttgc                                          24

<210> SEQ ID NO 14
<211> LENGTH: 23
<212> TYPE: DNA
<213> ORGANISM: Artificial Sequence
<220> FEATURE:
<223> OTHER INFORMATION: oligonucleotide SDR_seqR4

<400> SEQUENCE: 14
acatggtgct ggttcatgac tag                                           23

<210> SEQ ID NO 15
<211> LENGTH: 23
<212> TYPE: DNA
<213> ORGANISM: Artificial Sequence
<220> FEATURE:
<223> OTHER INFORMATION: oligonucleotide SDR_seqR5

<400> SEQUENCE: 15
tctagcacca agttctcttg ctg                                           23

<210> SEQ ID NO 16
<211> LENGTH: 17
<212> TYPE: DNA
<213> ORGANISM: Artificial Sequence
<220> FEATURE:
<223> OTHER INFORMATION: oligonucleotide M13 (-21)

<400> SEQUENCE: 16
tgtaaaacga cggccag                                                  17

<210> SEQ ID NO 17
<211> LENGTH: 419
<212> TYPE: DNA
<213> ORGANISM: Clostridium autoethanogenum

<400> SEQUENCE: 17
```

```
agaaattttc ctttctaaaa tattttattc catgtcaaga actctgttta tttcattaaa      60
gaactataag tacaaagtat aaggcatttg aaaaaatagg ctagtatatt gattgattat     120
ttattttaaa atgcctaagt gaaatatata catattataa caataaaata agtattagtg     180 taggatttt  aaatagagta tctatttca  gattaaattt ttgattattt gatttacatt     240
atataatatt gagtaaagta ttgactagca aaattttttg atactttaat ttgtgaaatt     300
tcttatcaaa agttatattt tgaataatt  tttattgaaa atacaacta  aaaaggatta     360 tagtataagt gtgtgtaatt ttgtgttaaa tttaaggga  ggaaatgaac atgaaattg      419
```

```
<210> SEQ ID NO 18
<211> LENGTH: 864
<212> TYPE: DNA
<213> ORGANISM: Clostridium autoethanogenum

<400> SEQUENCE: 18
```

```
atgaaaggaa gctcttatat ggaaaaatta gaaaaggttc aaaaaatttt taataaaaaa      60
tttgagagta aaagtgcgtg ggatagggtt actttagcta gaatgataga aaggccaact     120
tcacttgatt atataaatag aatatttgac tcttttatgg agcttcatgg agatagagat     180
tttaatgacg atccttctgt agtaggaggc attggattgt taaatggtga gcctgtaacc     240
attgtggccc agcaaaaagg taggaataca caggagaata aaagagaaaa ttttggtatg     300
ccggagcctg acggatatag aaaaggatta agactcatga agcaggcaga taaatttgat     360
aggcctatta tatgttttgt ggatacacct ggagcttttt gcggcatgga agcagaggaa     420
agaggacagg gagaggcaat agccaaaaat ctgatggaga tgtttaattt aagagtacct     480
ataatatcta atagttggag agaaggtgga agcggaggtg ctcttgcttt tgctgtagcg     540
gattcagttt ggatgctgga gaattctata tattctattt taaccccaga aggttttgca     600
ggtatactat ggaaagatgc ttccaaagct aaggaagcag ctgagattat gaaaattaca     660
gctcaagatt taaaaaaata cggtataata gataagatat aaaggaacc  tgcaggaggg     720 gcacaaaagg atgtagataa aatgtcctgc accataaaag aagaacttat agaaaaaata     780
ggcatactta ggaaaaggtc taagaggaa  ttacttgaac aaagatacaa taaatttaga     840
aaaatgggta agtttatgga atag                                            864
```

```
<210> SEQ ID NO 19
<211> LENGTH: 287
<212> TYPE: PRT
<213> ORGANISM: Clostridium autoethanogenum

<400> SEQUENCE: 19
```

Met Lys Gly Ser Ser Tyr Met Glu Lys Leu Glu Lys Val Gln Lys Ile
1               5                   10                  15

Phe Asn Lys Lys Phe Glu Ser Lys Ser Ala Trp Asp Arg Val Thr Leu
                20                  25                  30

Ala Arg Met Ile Glu Arg Pro Thr Ser Leu Asp Tyr Ile Asn Arg Ile
            35                  40                  45

Phe Asp Ser Phe Met Glu Leu His Gly Asp Arg Tyr Phe Asn Asp Asp
        50                  55                  60

Pro Ser Val Val Gly Gly Ile Gly Leu Leu Asn Gly Glu Pro Val Thr
65                  70                  75                  80

Ile Val Ala Gln Gln Lys Gly Arg Asn Thr Gln Glu Asn Ile Lys Arg
                85                  90                  95

Asn Phe Gly Met Pro Glu Pro Asp Gly Tyr Arg Lys Gly Leu Arg Leu

```
            100                 105                 110
Met Lys Gln Ala Asp Lys Phe Asp Arg Pro Ile Ile Cys Phe Val Asp
            115                 120                 125

Thr Pro Gly Ala Phe Cys Gly Met Glu Ala Glu Arg Gly Gln Gly
        130                 135                 140

Glu Ala Ile Ala Lys Asn Leu Met Glu Met Phe Asn Leu Arg Val Pro
145                 150                 155                 160

Ile Ile Ser Ile Ile Val Gly Glu Gly Ser Gly Gly Ala Leu Ala
                165                 170                 175

Phe Ala Val Ala Asp Ser Val Trp Met Leu Glu Asn Ser Ile Tyr Ser
            180                 185                 190

Ile Leu Thr Pro Glu Gly Phe Ala Gly Ile Leu Trp Lys Asp Ala Ser
        195                 200                 205

Lys Ala Lys Glu Ala Ala Glu Ile Met Lys Ile Thr Ala Gln Asp Leu
210                 215                 220

Lys Lys Tyr Gly Ile Ile Asp Lys Ile Leu Lys Glu Pro Ala Gly Gly
225                 230                 235                 240

Ala Gln Lys Asp Val Asp Lys Met Ser Cys Thr Ile Lys Glu Glu Leu
            245                 250                 255

Ile Glu Lys Ile Gly Ile Leu Arg Lys Arg Ser Lys Glu Glu Leu Leu
        260                 265                 270

Glu Gln Arg Tyr Asn Lys Phe Arg Lys Met Gly Lys Phe Met Glu
        275                 280                 285
```

<210> SEQ ID NO 20
<211> LENGTH: 876
<212> TYPE: DNA
<213> ORGANISM: Clostridium autoethanogenum

<400> SEQUENCE: 20

```
ttgttaaata aattctttaa aaaaacaaaa tatattacag ttagtcagag ggctttaaat      60
aatatccatg aagatttaga ttcaaagcca agtataccaa atggaatgtg gtaaaatgt     120
gatggatgtg gtaaggtact atataagcag gatctagaaa aaaataatag ggtatgccag    180
tattgcaagc atcattttag gatgaatgct aaagaaagaa tagatcttat aacagataag    240
gatagctttt gccaatttga tgaaaacatg acgtctacta atcctatagg atttaaagga    300
tatgaagata aaatcagcaa tatgcagaaa aagactaacc tcaaagaagc tgtaattaca    360
ggaaagggta ctataggagg agagtctgca gtaatttgtg ttatggatag taattttatg    420
atgggaagca tgggttccgt ggtaggagag aaaattacta gagctgtaga aaagctatt     480
gagttaaaaa tacctctaat tattttttaca gcttctggag gcgctagaat gcaggagggt    540
atttttttcat taatgcaaat ggcaaagata agtggagcta taaacaggtt gaatgatgca    600
ggacttttat atatatcggt tcttacagat cctactactg gtggagttac agcaagtttt    660
gctatgcttg gtgatataat tttagcagaa cctggagcac ttgttggatt tgcaggaaag    720
agagtaatag agcagaccat aaagcaaaaa cttcccgatg gatttcaaag tgcagaattt    780
ctattaaaac atggatttgt agatagtata gtttcaaggg aaaatttaaa gagtaccttg    840
aagaagatat tgtatattca taataggaat aggtaa                              876
```

<210> SEQ ID NO 21
<211> LENGTH: 291
<212> TYPE: PRT
<213> ORGANISM: Clostridium autoethanogenum

<400> SEQUENCE: 21

Met Leu Asn Lys Phe Phe Lys Lys Thr Lys Tyr Ile Thr Val Ser Gln
1               5                   10                  15

Arg Ala Leu Asn Asn Ile His Glu Asp Leu Asp Ser Lys Pro Ser Ile
            20                  25                  30

Pro Asn Gly Met Trp Val Lys Cys Asp Gly Cys Gly Lys Val Leu Tyr
        35                  40                  45

Lys Gln Asp Leu Glu Lys Asn Asn Arg Val Cys Gln Tyr Cys Lys His
    50                  55                  60

His Phe Arg Met Asn Ala Lys Glu Arg Ile Asp Leu Ile Thr Asp Lys
65                  70                  75                  80

Asp Ser Phe Cys Gln Phe Asp Glu Asn Met Thr Ser Thr Asn Pro Ile
                85                  90                  95

Gly Phe Lys Gly Tyr Glu Asp Lys Ile Ser Asn Met Gln Lys Lys Thr
            100                 105                 110

Asn Leu Lys Glu Ala Val Ile Thr Gly Lys Gly Thr Ile Gly Gly Glu
        115                 120                 125

Ser Ala Val Ile Cys Val Met Asp Ser Asn Phe Met Met Gly Ser Met
    130                 135                 140

Gly Ser Val Val Gly Glu Lys Ile Thr Arg Ala Val Glu Lys Ala Ile
145                 150                 155                 160

Glu Leu Lys Ile Pro Leu Ile Ile Phe Thr Ala Ser Gly Gly Ala Arg
                165                 170                 175

Met Gln Glu Gly Ile Phe Ser Leu Met Gln Met Ala Lys Ile Ser Gly
            180                 185                 190

Ala Ile Asn Arg Leu Asn Asp Ala Gly Leu Leu Tyr Ile Ser Val Leu
        195                 200                 205

Thr Asp Pro Thr Thr Gly Gly Val Thr Ala Ser Phe Ala Met Leu Gly
    210                 215                 220

Asp Ile Ile Leu Ala Glu Pro Gly Ala Leu Val Gly Phe Ala Gly Lys
225                 230                 235                 240

Arg Val Ile Glu Gln Thr Ile Lys Gln Lys Leu Pro Asp Gly Phe Gln
                245                 250                 255

Ser Ala Glu Phe Leu Leu Lys His Gly Phe Val Asp Ser Ile Val Ser
            260                 265                 270

Arg Glu Asn Leu Lys Ser Thr Leu Lys Lys Ile Leu Tyr Ile His Asn
        275                 280                 285

Arg Asn Arg
    290

<210> SEQ ID NO 22
<211> LENGTH: 1344
<212> TYPE: DNA
<213> ORGANISM: Clostridium autoethanogenum

<400> SEQUENCE: 22
gtgtttaata agattttgat tgccaataga ggagaaatag cagttaggat aattagagct    60
tgcagggaaa tgggaataga aactgtagca gtgtattcag aagcagatag ggatgcactt   120
catactcaga tggcggatga agccatatgt ataggaccgg catctcctaa agaaagttat   180
ttaaacgtac aaaatataat aagtgccaca gttttatcag gagcgcaagc tattcatcct   240
ggatttggtt ttttatctga aaacagtaag tttgcaagta tatgtaaaca gtgtaatatt   300
acttttatag gccctactcc ggaatgtatt gacaatatgg gcaataagtc taatgctaga   360

```
gatataatgg gaaaggcagg agttcctatc gttccagggt cagatggtgc tataaaaaca    420
aatgaagaac ttttggaaac tgcaagaaaa ataggatatc ctgttatgat aaaagcctct    480
gcaggcggtg gtggacgtgg tataagagtc gtatatgatg aatctgagat tataaaaaat    540
tatgaaaatg ctaaagctga agctagtgca gcctttggag atgacactat atacttagaa    600
aagtttatag aaagaccaaa gcatgtagaa attcagatac ttggagataa ttttgaaaat    660
gtagtttatc tgggggaaag agactgttcc atgcagagaa gaaatcaaaa agtaatggaa    720
gaagcaccta gcaaggtagt tacggaagaa cttagaaaat ccatgggaga aacagctgta    780
agggcagcca aggctgtaca ttataataat gctggaactg tagaatttct tttagacaaa    840
aataataatt actatttcat ggagatgaat actcgtattc aagtagaaca tgctataaca    900
gaaatggtaa caggtataga tcttgtaaaa gaacagataa aaattgcagc aggagaaaag    960
ttagattttt ctcaagagga tgttaagata accggtcatt ctatagaatg cagaataaat    1020
gcagaagatg taaaagagg ttttatgcct ctccaggaa agataaaaga cttatatgta    1080
cctggaggtt ttaatgtaag agtagatagt gcagtgtact cgggatataa tattcctccc    1140
tattatgatt ctatgatagc aaagctcatt gtatatggaa aagataggga tgaggctata    1200
tgcagaatga ggagagcctt gggagagttt attataagaa gggttagtac caatatagac    1260
ttccaatttg aactcataga tagtaaggaa tttatagaag aacttatga tacaaagttt    1320 atagaaaata atttcaagta ttaa                                          1344
```

<210> SEQ ID NO 23
<211> LENGTH: 447
<212> TYPE: PRT
<213> ORGANISM: Clostridium autoethanogenum

<400> SEQUENCE: 23

```
Met Phe Asn Lys Ile Leu Ile Ala Asn Arg Gly Glu Ile Ala Val Arg
1               5                   10                  15

Ile Ile Arg Ala Cys Arg Glu Met Gly Ile Glu Thr Val Ala Val Tyr
            20                  25                  30

Ser Glu Ala Asp Arg Asp Ala Leu His Thr Gln Met Ala Asp Glu Ala
        35                  40                  45

Ile Cys Ile Gly Pro Ala Ser Pro Lys Glu Ser Tyr Leu Asn Val Gln
    50                  55                  60

Asn Ile Ile Ser Ala Thr Val Leu Ser Gly Ala Gln Ala Ile His Pro
65                  70                  75                  80

Gly Phe Gly Phe Leu Ser Glu Asn Ser Lys Phe Ala Ser Ile Cys Lys
                85                  90                  95

Gln Cys Asn Ile Thr Phe Ile Gly Pro Thr Pro Glu Cys Ile Asp Asn
            100                 105                 110

Met Gly Asn Lys Ser Asn Ala Arg Asp Ile Met Gly Lys Ala Gly Val
        115                 120                 125

Pro Ile Val Pro Gly Ser Asp Gly Ala Ile Lys Thr Asn Glu Glu Leu
    130                 135                 140

Leu Glu Thr Ala Arg Lys Ile Gly Tyr Pro Val Met Ile Lys Ala Ser
145                 150                 155                 160

Ala Gly Gly Gly Gly Arg Gly Ile Arg Val Val Tyr Asp Glu Ser Glu
                165                 170                 175

Ile Ile Lys Asn Tyr Glu Asn Ala Lys Ala Glu Ala Ser Ala Ala Phe
            180                 185                 190

Gly Asp Asp Thr Ile Tyr Leu Glu Lys Phe Ile Glu Arg Pro Lys His
```

```
                195                 200                 205
Val Glu Ile Gln Ile Leu Gly Asp Asn Phe Glu Asn Val Val Tyr Leu
    210                 215                 220

Gly Glu Arg Asp Cys Ser Met Gln Arg Arg Asn Gln Lys Val Met Glu
225                 230                 235                 240

Glu Ala Pro Ser Lys Val Val Thr Glu Leu Arg Lys Ser Met Gly
                245                 250                 255

Glu Thr Ala Val Arg Ala Ala Lys Ala Val His Tyr Asn Asn Ala Gly
            260                 265                 270

Thr Val Glu Phe Leu Leu Asp Lys Asn Asn Tyr Tyr Phe Met Glu
                275                 280                 285

Met Asn Thr Arg Ile Gln Val Glu His Ala Ile Thr Glu Met Val Thr
    290                 295                 300

Gly Ile Asp Leu Val Lys Glu Gln Ile Lys Ile Ala Ala Gly Glu Lys
305                 310                 315                 320

Leu Asp Phe Ser Gln Glu Asp Val Lys Ile Thr Gly His Ser Ile Glu
                325                 330                 335

Cys Arg Ile Asn Ala Glu Asp Val Lys Arg Gly Phe Met Pro Ser Pro
            340                 345                 350

Gly Lys Ile Lys Asp Leu Tyr Val Pro Gly Gly Phe Asn Val Arg Val
                355                 360                 365

Asp Ser Ala Val Tyr Ser Gly Tyr Asn Ile Pro Pro Tyr Tyr Asp Ser
370                 375                 380

Met Ile Ala Lys Leu Ile Val Tyr Gly Lys Asp Arg Asp Glu Ala Ile
385                 390                 395                 400

Cys Arg Met Arg Arg Ala Leu Gly Glu Phe Ile Ile Glu Gly Val Ser
                405                 410                 415

Thr Asn Ile Asp Phe Gln Phe Glu Leu Ile Asp Ser Lys Glu Phe Ile
            420                 425                 430

Glu Gly Thr Tyr Asp Thr Lys Phe Ile Glu Asn Asn Phe Lys Tyr
                435                 440                 445

<210> SEQ ID NO 24
<211> LENGTH: 513
<212> TYPE: DNA
<213> ORGANISM: Clostridium autoethanogenum

<400> SEQUENCE: 24
atggacttta aagcaattga gaatatgata aaaactatgg ataattcaaa gcttggatat      60
ttagaagtta ttgggataac gtatcctata attatgaaaa agcagggtga agaaggaaat    120
ataaaacagg taacatagt  aaaggaaat  ggagaaaatg taaaacctgt ctttgaaaaa    180
caaagtgaca aaattgaagc aaaagaagat aatatagata aggtaaaaaa agttgaagaa    240
aaaaaagatg atgatataga ggacagcaat ataaagaag  taaagtcacc tatagtaggt    300 acttttttaca attcatcagg acctgaaaaa cctgttttttg taaatgtagg atctaaggta    360
aaaaaaggag acactctgtg tataatagaa gctatgaaac ttatgaatga gattcaaagc    420
gaggtagatg gagaagtagt ggatatttta gttaagaatg aacagatggt agagtatggc    480
cagccgctat ttaaaataaa aactgaatct taa                                 513

<210> SEQ ID NO 25
<211> LENGTH: 170
<212> TYPE: PRT
<213> ORGANISM: Clostridium autoethanogenum
```

<400> SEQUENCE: 25

```
Met Asp Phe Lys Ala Ile Glu Asn Met Ile Lys Thr Met Asp Asn Ser
1               5                   10                  15

Lys Leu Gly Tyr Leu Glu Val Asn Trp Asp Asn Val Ser Ile Ile Met
            20                  25                  30

Lys Lys Gln Gly Glu Gly Asn Ile Lys Gln Val Asn Ile Val Lys
        35                  40                  45

Gly Asn Gly Glu Asn Val Lys Pro Val Phe Glu Lys Gln Ser Asp Lys
50                  55                  60

Ile Glu Ala Lys Glu Asp Asn Ile Asp Lys Val Lys Lys Val Glu Glu
65                  70                  75                  80

Lys Lys Asp Asp Asp Ile Glu Asp Ser Asn Ile Lys Glu Val Lys Ser
                85                  90                  95

Pro Ile Val Gly Thr Phe Tyr Asn Ser Ser Gly Pro Glu Lys Pro Val
            100                 105                 110

Phe Val Asn Val Gly Ser Lys Val Lys Lys Gly Asp Thr Leu Cys Ile
            115                 120                 125

Ile Glu Ala Met Lys Leu Met Asn Glu Ile Gln Ser Glu Val Asp Gly
130                 135                 140

Glu Val Val Asp Ile Leu Val Lys Asn Glu Gln Met Val Glu Tyr Gly
145                 150                 155                 160

Gln Pro Leu Phe Lys Ile Lys Thr Glu Ser
                165                 170
```

<210> SEQ ID NO 26
<211> LENGTH: 1806
<212> TYPE: DNA
<213> ORGANISM: Artificial Sequence
<220> FEATURE:
<223> OTHER INFORMATION: designed Type II methyltransferase

<400> SEQUENCE: 26

```
atgtttccgt gcaatgccta tatcgaatat ggtgataaaa atatgaacag ctttatcgaa    60
gatgtggaac agatctacaa cttcattaaa aagaacattg atgtggaaga aaagatgcat   120
ttcattgaaa cctataaaca gaaaagcaac atgaagaaag agattagctt tagcgaagaa   180
tactataaac agaagattat gaacggcaaa aatggcgttg tgtacacccc gccggaaatg   240
gcggccttta tggttaaaaa tctgatcaac gttaacgatg ttattggcaa tccgtttatt   300
aaaatcattg acccgagctg cggtagcggc aatctgattt gcaaatgttt tctgtatctg   360
aatcgcatct ttattaagaa cattgaggtg attaacagca aaaataacct gaatctgaaa   420
ctggaagaca tcagctacca catcgttcgc aacaatctgt ttggcttcga tattgacgaa   480
accgcgatca aagtgctgaa aattgatctg tttctgatca gcaaccaatt tagcgagaaa   540
aatttccagg ttaaagactt tctggtggaa atattgatc gcaaatatga cgtgttcatt   600
ggtaatccgc cgtatatcgg tcacaaaagc gtggacagca gctacagcta cgtgctgcgc   660
aaaatctacg gcagcatcta ccgcgacaaa ggcgatatca gctattgttt ctttcagaag   720
agcctgaaat gtctgaagga agtggcaaa ctggtgtttg tgaccagccg ctacttctgc   780
gagagctgca gcgtaaaga actgcgtaaa ttcctgatcg aaaacacgag catttacaag   840
atcattgatt tttacggcat ccgcccgttc aaacgcgtgg gtatcgatcc gatgattatt   900
tttctggttc gtacgaagaa ctggaacaat aacattgaaa ttattcgccc gaacaagatt   960
gaaaagaacg aaaagaacaa attcctggat agcctgttcc tggacaaaag cgaaaagtgt  1020
```

```
aaaaagttta gcattagcca gaaaagcatt aataacgatg gctgggtttt cgtggacgaa    1080
gtggagaaaa acattatcga caaaatcaaa gagaaaagca agttcattct gaaagatatt    1140
tgccatagct gtcaaggcat tatcaccggt tgtgatcgcg cctttattgt ggaccgtgat    1200
atcatcaata gccgtaagat cgaactgcgt ctgattaaac cgtggattaa aagcagccat    1260
atccgtaaga atgaagttat taagggcgaa aaattcatca tctatagcaa cctgattgag    1320
aatgaaaccg agtgtccgaa tgcgattaaa tatatcgaac agtacaagaa acgtctgatg    1380
gagcgccgcg aatgcaaaaa gggcacgcgt aagtggtatg aactgcaatg gggccgtaaa    1440
ccggaaatct tcgaagaaaa gaaaattgtt ttcccgtata aaagctgtga caatcgtttt    1500
gcactggata agggtagcta ttttagcgca gacatttata gcctggttct gaagaaaaat    1560
gtgccgttca cctatgagat cctgctgaat atcctgaata gcccgctgta cgagttttac    1620
tttaagacct tcgcgaaaaa gctgggcgag aatctgtacg agtactatcc gaacaacctg    1680
atgaagctgt gcatcccgag catcgatttc ggcggtgaga acaatattga gaaaaagctg    1740
tatgatttct ttggtctgac ggataaagaa attgagattg tggagaagat caaagataac    1800
tgctaa                                                               1806
```

RECOMBINANT MICROORGANISMS AND USES THEREFOR

CROSS REFERENCE TO RELATED APPLICATIONS

This application claims the benefit of U.S. Patent Application 61/653,348 filed May 30, 2012, the entirety of which is incorporated herein by reference.

TECHNICAL FIELD OF THE INVENTION

The present invention relates to recombinant microorganisms and methods for the production of 3-Hydroxypropionate [3-HP] by microbial fermentation of a substrate comprising CO and/or $CO_2$.

BACKGROUND OF THE INVENTION

3-Hydroxypropionate [3-HP] is a platform chemical, acting as precursor for production of polymer materials and as chemical feedstock. Poly(3-hydroxypropionicacid) [P(3-HP)] is a biodegradable polymer with promising characteristics such as unusual high heat stability.

3-HP can be used to derive a number of valuable industrial chemicals including: acrylic acid which is used in the manufacture of paint, paper, adhesives, textiles, specialty coatings, ink, and superabsorbent polymer polyacrylates; 1,3-propanediol which is of use as a solvent, adhesive, cosmetic, or to make polytrimethylene terephthalate used in carpet and textiles; 3-hydroxypropinaldehyde which is used in the preparation of foods, as a feed additive, and as a preservative in the nutritional industry.

3-HP is listed as third most important renewable chemical by the US department of energy and a global market opening for 3-HP has been estimated to be 3.63 million tons per year (Paster et al, 2003, US DOE report: 48-49).

It is an object of the invention to provide recombinant microorganisms and a method for the production of 3-HP by microbial fermentation which may provide one or more advantages over known methods, or to at least to provide the public with a useful choice.

SUMMARY OF INVENTION

The invention generally provides, inter alia, methods for the production of 3-HP by microbial fermentation of a substrate comprising CO and/or $CO_2$, and recombinant microorganisms of use in such methods. It combines two different $CO_2$ fixation pathways to produce a single metabolic product.

In a first aspect, the invention provides an anaerobic acetogenic recombinant microorganism capable of producing 3-HP and optionally one or more other products by fermentation of a substrate comprising CO and/or $CO_2$.

In one particular embodiment, the microorganism is adapted to express one or more enzymes (or one or more subunits thereof) in the 3-HP biosynthesis pathway which enzymes are not naturally present in a parental microorganism from which the recombinant microorganism is derived. In another embodiment, the microorganism is adapted to over-express one or more enzymes (or one or more subunits thereof) in the 3-HP biosynthesis pathway, which enzymes are naturally present in a parental microorganism from which the recombinant microorganism is derived. In one embodiment, the microorganism is adapted to express one or more enzymes (or one or more subunits thereof) in the 3-HP-biosynthesis pathway which are not naturally present in a parental microorganism and over-express one or more enzymes (or one or more subunits thereof) in the 3-HP biosynthesis pathway which are naturally present in a parental microorganism.

In one embodiment, the one or more enzymes are chosen from the group consisting of: Malonyl-CoenzymeA reductase (EC 1.2.1.75); Acetyl-CoA Carboxylase (ACC) (EC 6.4.1.2); and a functionally equivalent variant of any one thereof.

In one embodiment, the parental microorganism is capable of fermenting a substrate comprising CO and/or $CO_2$ to produce Acetyl-CoA but not of converting Acetyl-CoA to 3-HP and the recombinant microorganism is adapted to express one or more enzymes (or one or more subunits thereof) involved in the conversion of Acetyl-CoA to 3-HP.

In one embodiment, the microorganism comprises one or more exogenous nucleic acids adapted to increase expression of one or more nucleic acids native to the parental microorganism and which one or more nucleic acids encode one or more of the enzymes (or one or more subunits thereof) referred to herein before.

In one embodiment, the one or more exogenous nucleic acid adapted to increase expression is a regulatory element. In one embodiment, the regulatory element is a promoter.

In one embodiment, the promoter is a constitutive promoter. In one embodiment, the promoter is selected from the group comprising Wood-Ljungdahl gene cluster or Phosphotransacetylase/Acetate kinase operon promoters.

In one embodiment, the microorganism comprises one or more exogenous nucleic acids encoding and adapted to express one or more of the enzymes (or one or more subunits thereof) referred to herein before. In one embodiment, the microorganisms comprise one or more exogenous nucleic acid encoding and adapted to express at least two of the enzymes (or one or more subunits thereof).

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid.

In one embodiment, the parental microorganism is selected from the group of anaerobic acetogens.

In one particular embodiment, the parental microorganism is selected from the group of carboxydotrophic acetogenic bacteria, in one embodiment from the group comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kiuvi*.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes encoding Malonyl-CoenzymeA reductase and/or Acetyl-CoA carboxylase, or one or more subunits thereof.

In a second aspect, the invention provides a nucleic acid encoding one or more enzymes (or one or more subunits thereof) which when expressed in a microorganism allows the microorganism to produce 3-HP by fermentation of substrate comprising CO and/or $CO_2$.

In one embodiment, the nucleic acid encodes two or more enzymes (or one or more subunits thereof) which when expressed in a microorganism allows the microorganism to produce 3-HP by fermentation of substrate comprising CO.

In one embodiment, the enzymes are chosen from Malonyl-CoenzymeA reductase and Acetyl CoA carboxylase, and a functionally equivalent variant of any one or more thereof.

In one embodiment, the nucleic acid comprises nucleic acid sequences encoding Malonyl-CoenzymeA reductase, Acetyl CoA carboxylase, or a functionally equivalent variant of any one or more thereof, in any order.

In one embodiment, the nucleic acid encoding Malonyl-CoenzymeA reductase has the sequence of SEQ ID NO: 1 or GI:163848165, Caur 2614, or is a functionally equivalent variant thereof.

In one embodiment, the nucleic acid encoding Acetyl CoA carboxylase comprises the sequences SEQ ID NO: 18, 20, 22, and 24 (or CLJU c42100-40, GI: 9447826-31, GI:163847210-11, Caur_1647-48, GI:163849262, Caur_3739, GI:163848951, Caur_3421, GI:163846951, Caur_1378), or a functionally equivalent variant of any one or more thereof. Acetyl CoA carboxylase may be comprised of a number of subunits. These may be encoded on one or more nucleic acids, if desired.

In one embodiment, the nucleic acids of the invention further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum*.

In a third aspect, the invention provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the invention provides host organisms comprising any one or more of the nucleic acids of the seventh aspect or vectors or constructs of the third aspect.

In a fifth aspect, the invention provides a composition comprising an expression construct or vector as referred to in the third aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In a sixth aspect, the invention provides a method for the production of 3-HP, and optionally one or more other products, by microbial fermentation comprising fermenting a substrate comprising CO and/or $CO_2$ using a recombinant microorganism of the first aspect of the invention.

In one embodiment the method comprises the steps of:
(a) providing a substrate comprising CO and/or $CO_2$ to a bioreactor containing a culture of one or more microorganism of the first aspect of the invention; and
(b) anaerobically fermenting the culture in the bioreactor to produce 3-HP.

In one embodiment the method comprises the steps of:
(a) capturing CO— and/or $CO_2$-containing gas produced as a result of the industrial process, before the gas is released into the atmosphere;
(b) the anaerobic fermentation of the CO— and/or $CO_2$-containing gas to produce at least 3-HP by a culture containing one or more microorganism of the first aspect of the invention.

In particular embodiments of the method aspects, the microorganism is maintained in an aqueous culture medium.

In particular embodiments of the method aspects, the fermentation of the substrate takes place in a bioreactor.

Preferably, the substrate comprising CO and/or $CO_2$ is a gaseous substrate comprising CO and/or $CO_2$. In one embodiment, the substrate comprises an industrial waste gas. In certain embodiments, the gas is steel mill waste gas or syngas.

In a particular embodiment, the substrate is a substrate comprising CO.

In embodiments of the invention where the substrate comprises $CO_2$, but no CO, the substrate preferably also comprises $H_2$.

In one embodiment, the substrate comprises CO and $CO_2$. In one embodiment, the substrate comprises $CO_2$ and $H_2$. In another embodiment, the substrate comprises CO, $CO_2$, and $H_2$.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering 3-HP and optionally one or more other products from the fermentation broth.

In a seventh aspect, the invention provides 3-HP when produced by the method of the sixth aspect.

In another aspect, the invention provides a method for the production of a microorganism of the first aspect of the invention comprising transforming a parental microorganism with one or more exogenous nucleic acid such that the microorganism is capable of producing 3-HP, and optionally one or more other products, by fermentation of a substrate comprising CO and/or $CO_2$, wherein the parental microorganism is not capable of producing 3-HP by fermentation of a substrate comprising CO and/or $CO_2$.

In one particular embodiment, a parental microorganism is transformed with one or more exogenous nucleic acid adapted to express one or more enzymes in the 3-HP biosynthesis pathway which are not naturally present in the parental microorganism. In another embodiment, a parental microorganism is transformed with one or more nucleic acid adapted to over-express one or more enzymes in the 3-HP biosynthesis pathway which are naturally present in the parental microorganism. In another embodiment, a parental microorganism is transformed with one or more exogenous nucleic acid adapted to express one or more enzymes in the 3-HP biosynthesis pathway which are not naturally present in the parental microorganism and over-express one or more enzymes in the 3-HP biosynthesis pathway which are naturally present in the parental microorganism.

In certain embodiments, the one or more enzymes are as herein before described.

In certain embodiment, the parental microorganism is as herein before described.

According to one embodiment a process is provided for converting CO or CO2 into 3-hydroxypropionate (3-HP). A gaseous CO-containing and/or CO2-containing substrate is passed to a bioreactor containing a culture of carboxydotrophic, acetogenic bacteria in a culture medium such that the bacteria convert the CO and/or CO2 to 3-HP. The carboxydotrophic acetogenic bacteria are genetically engineered to express a malonyl-Coenzyme A reductase. They also express an acetyl-CoA carboxylase, whether native or exogenous. The 3-HP is recovered from the bioreactor.

According to another embodiment an isolated, genetically engineered, carboxydotrophic, acetogenic bacterium is provided that comprises a nucleic acid encoding a malonyl-Coenzyme A reductase. The nucleic acid is exogenous to the host bacteria. The bacteria express the malonyl-Coenzyme A reductase and the bacteria acquire the ability to fix three molecules of CO or CO2 into one molecule of 3-hydroxypropionate (3-HP). The malonyl-Coenzyme A reductase is typically at least 85% identical to the amino acid sequence encoded by the nucleotide sequence of SEQ ID NO: 1.

The bacteria may further comprise an exogenous nucleic acid encoding acetyl-Coenzyme A carboxylase. The acetyl-CoA carboxylase is typically at least 85% identical to the amino acid sequence encoded by the nucleotide sequence of SEQ ID NO: 18-21. The nucleic acid may be operably linked to a promoter. The nucleic acid may have been codon optimized. The nucleic acid or the encoded carboxylase may be from a nonsulfur, photosynthetic bacterium. The bacteria may be selected from the group consisting of *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kiuvi*. The donor bacterium of the exogenous nucleic acid may be a nonsulfur, photosynthetic bacterium such as, *Chloroflexus auranticus, Metallosphaera,* and *Sulfolobus* spp.

The genetically engineered bacteria may be cultured by growing in a medium comprising a gaseous carbon source. The carbon source may comprise CO and/or CO2, which may be used as either or both of an energy source or a carbon source. The bacteria may optionally be grown under strictly anaerobic conditions. The carbon source may comprise an industrial waste product or off-gas.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

These and other aspects of the present invention, which should be considered in all its novel aspects, will become apparent from the following description, which is given by way of example only, with reference to the accompanying figures, in which:

FIG. 1: Combination of two $CO_2$ fixing pathways for sustainable production of 1 molecule 3-HP from 3 molecules of CO or $CO_2$.

DETAILED DESCRIPTION OF THE PREFERRED EMBODIMENTS

The following description of preferred embodiments is given in general terms. The invention is further elucidated from the disclosure given under the heading "Examples" herein below, which provides experimental data supporting the invention, specific examples of various aspects of the invention, and means of performing the invention.

The inventors have surprisingly been able to engineer a carboxydotrophic acetogenic microorganism to produce 3-Hydroxypropionate (3-HP) by fermentation of a substrate comprising CO and/or $CO_2$. This offers an alternative means for the production of 3-HP which may have benefits over the current methods for the production of 3-HP. In addition, it offers a means of using carbon monoxide from industrial processes which would otherwise be released into the atmosphere and pollute the environment.

In engineering the microorganisms of the invention, the inventors have surprisingly been able to combine two separate $CO_2$ fixation pathways, as illustrated in FIG. 1. This provides for sustainable fermentation to produce 3-HP using a substrate comprising CO and/or a substrate comprising $CO_2$. Two pathways fixing $CO_2$ are thus linked to produce a desired product.

In one embodiment, the invention describes fixation of three molecules of CO2 into one molecule of 3-HP by combining two separate CO2 fixation pathways (FIG. 1), the Wood-Ljungdahl pathways of acetogens that allows fixation of two molecules of CO2, and the initial carbon fixation steps of the 3-HP cycle allows fixation of another molecule of CO2. CO2 could also be replaced with carbon monoxide (CO), as the key enzyme of the Wood-Ljungdahl pathway, a CO dehydrogenase (CODH) is able to convert CO into CO2 and energy in a biological water gas shift reaction (CO+ H2O<->CO2+H2). Any mixture of CO and CO2 can be used. When CO2 alone is used, energy in form of Hydrogen or electricity may need to be supplied, while CO can serve as both carbon and energy source.

While the inventors have demonstrated the efficacy of the invention in *Clostridium autoethanogenum*, the invention is applicable to the wider group of anaerobic acetogenic microorganisms and fermentation on substrates comprising CO and/or $CO_2$, as discussed above and further herein.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism. This is also called a host microorganism.

The term "main fermentation product" is intended to mean the one fermentation product which is produced in the highest concentration and/or yield. There may be one or more fermentation products. The most prevalent may or may not be the most commercially valuable.

The terms "increasing the efficiency," "increased efficiency," and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for a substrate comprising CO to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

The phrase "substrate comprising carbon dioxide" and like terms should be understood to include any substrate in which carbon dioxide is available to one or more strains of bacteria for growth and/or fermentation, for example. Substrates comprising carbon dioxide may further comprise hydrogen and/or carbon monoxide.

The phrase "gaseous substrate comprising carbon dioxide" and like phrases and terms includes any gas which contains a level of carbon dioxide. In certain embodiments the substrate contains at least about 10% to about 60% $CO_2$ by volume, from 20% to 50% $CO_2$ by volume, from 30% to 60% $CO_2$ by volume, and from 40% to 55% $CO_2$ by volume. In particular embodiments, the substrate comprises about 20%, or about 25%, or about 30%, or about 35%, or about 40%, or about 45%, or about 50% CO, or about 55% CO, or about 60% $CO_2$ by volume.

Preferably, a substrate comprising $CO_2$ will also contain a level of CO or $H_2$. In particular embodiments, the substrate comprises a $CO_2$:$H_2$ ratio of at least about 1:1, or at least about 1:2, or at least about 1:3, or at least about 1:4, or at least about 1:5.

In the description which follows, embodiments of the invention are described in terms of delivering and fermenting a "gaseous substrate containing CO and/or $CO_2$." However, it should be appreciated that the gaseous substrate may be provided in alternative forms. For example, the gaseous substrate containing CO and/or $CO_2$ may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO and/or $CO_2$" and the like.

In particular embodiments of the invention, the CO-containing gaseous substrate (or a gaseous substrate comprising $CO_2$, or CO and $CO_2$, or $CO_2$ and $H_2$ and CO) is an industrial off or waste gas. "Industrial waste or off gases" should be taken broadly to include any gases comprising CO and/or $CO_2$ produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of microorganisms which differ from the organism to which they are to be introduced, or they may be artificially or recombinantly created. When an organism is genetically engineered or recombinant, it contains sequences that are adjacent to different sequences than in the naturally occurring microorganism. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state. The exogenous sequence may come from a heterologous source, for example, another species, genus, family, or kingdom. In any event, the bacterium so produced is non-naturally occurring, having a genetic complement which is different from the naturally occurring, either by sequence differences or by copy number differences, for example.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants." By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein.

These include homologous genes in species such as *Clostridium ljungdahlii, Chloroflexus auranticus, Metallosphaera* or *Sulfolobus* spp, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants." A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods outlined by Hügler et al (2002, *J. Bacteriol.* 184: 2404-2410 or Kroeger et al (2011, *Anal. Biochem.* 411: 100-5) may be used to measure the activity of Malonyl-coenzyme A reductase and Acetyl Co-A carboxylase, respectively.

"Over-express," "over expression," and like terms and phrases when used in relation to the invention should be taken broadly to include any increase in expression of one or more protein as compared to the expression level of the protein of a parental microorganism under the same conditions. It should not be taken to mean that the protein is expressed at any particular level.

A "parental microorganism" is a microorganism used to generate a recombinant microorganism of the invention. The parental microorganism may be one that occurs in nature (i.e., a wild type microorganism) or one that has been previously modified but which does not express or over-express one or more of the enzymes the subject of the present invention. Accordingly, the recombinant microorganisms of the invention have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

The "3-HP biosynthesis pathway" is the enzymatic pathway allowing for the conversion of Acetyl-CoA to Malonyl-CoA to Malonate semialdehyde to 3-HP. Unless the context clearly requires otherwise, reference to an enzyme in the 3-HP biosynthesis pathway should be taken to include reference to any one or more subunits of the enzyme. By way of example only, Acetyl CoA carboxylase may comprise four subunits.

Microorganisms

As discussed herein before, the invention provides a recombinant microorganism capable of producing 3-HP, and optionally one or more other products, by fermentation of a substrate comprising CO and/or $CO_2$.

In one particular embodiment, the microorganism is adapted to express one or more enzymes (or one or more subunits thereof) in the 3-HP biosynthesis pathway which are not naturally present in a parental microorganism from which it is derived. In another embodiment, the microorganism is adapted to over-express one or more enzymes (or one or more subunits thereof) in the 3-HP biosynthesis pathway which are naturally present in the parental microorganism.

In one embodiment, the parental microorganism is capable of fermenting a substrate comprising CO to produce Acetyl-CoA but not of converting Acetyl-CoA to 3-HP and the recombinant microorganism is adapted to express one or more enzymes (or one or more subunits thereof) involved in the conversion of Acetyl-CoA to 3-HP. In one embodiment, the parental microorganism is capable of converting Acetyl CoA to Malonyl CoA, but not of converting Malonyl CoA to 3-HP. In another embodiment, the parental microorganism is capable of converting Malonyl CoA to 3-HP but not of converting Acetyl CoA to Malonyl CoA.

In one embodiment the one or more enzymes in the 3-HP biosynthesis pathway are chosen from the group consisting: Malonyl-coenzyme A reductase; Acetyl CoA carboxylase; and a functionally equivalent variant of any one or more thereof.

The microorganism may be adapted to express or over-express the one or more enzymes (or one or more subunits thereof) by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not naturally present within the parental microorganism.

In certain embodiments, the parental microorganism may be transformed to provide a combination of increased or over-expression of one or more genes native to the parental microorganism and introduction of one or more genes not native to the parental microorganism. For example, one or more genes encoding one or more enzyme in the 3-HP biosynthesis pathway may be native to the parental microorganism but it may not include one or more other genes encoding one or more other enzyme in the pathway. The microorganism could for example be engineered to over-express native Acetyl CoA carboxylase and to introduce a Malonyl CoA reductase gene encoding an enzyme for the conversion of Malonyl-CoA to 3-HP (e.g., Malonyl CoA reductase). Alternatively, the microorganism could be engineered to over-express native Malonyl CoA reductase and to introduce a gene encoding Acetyl CoA carboxylase. Skilled persons will appreciate various other combinations of use in the invention.

By way of example only, exemplary sequence information for Malonyl CoA reductase is provided in the form of SEQ ID NO: 1 herein, and also on public databases with the accession numbers YP_001636209.1/Caur_2614, GI:163848165. By way of additional example, exemplary sequence information for Acetyl CoA carboxylase is provided in the form of SEQ ID NO: 18-21 herein, and also on public databases with the accession numbers NC 014328.1-33.1/CLJU_c42100-40, GI: 9447826-31, and GI:163847210-11, Caur_1647-48, YP_001635254.1-55.1; GI:163849262, Caur_3739, YP_001637306.1; GI:163848951, Caur_3421, YP_001636995.1; GI:163846951, Caur_1378, YP_001634995.1. Naturally occurring or synthetic enzymes may be used. Typically the enzymes will have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, identity with the sequence encoded by a nucleic acid according to SEQ ID NO:1 or 18-21.

The enzymes (and any corresponding genes encoding them) of use in the microorganisms of the invention may be derived from any appropriate source, including different genera and species of bacteria, or other organisms. However, in one embodiment, the Malonyl-coenzymeA reductase is that derived from *Chloroflexus auranticus, Clostridium ljungdahlii, Metallosphaera* or *Sulfolobus* spp. In one embodiment, the Malonyl-coenzyme A reductase has the amino acid sequence exemplified above, or it is a functionally equivalent variant thereof. In one embodiment, the Acetyl CoA carboxylase is that derived from *Clostridium ljungdahlii, Chloroflexus auranticus, Metallosphaera* or *Sulfolobus* spp. In one embodiment, the Acetyl CoA carboxylase has the amino acid sequence exemplified herein before, or it is a functionally equivalent variant thereof.

Malonyl-CoA reductase (EC 1.2.1.75) belongs to the group of short-chain reductases (SDRs) and can be obtained from bacteria as green non-sulfur phototrophic bacteria (Chloroflexi) *Chloroflexus aurantiacus* (YP_001636209.1; AAS20429.1), *Chloroflexus aggregans* (YP 002462600.1), *Oscillochloris trichoides* (WP_066561105.1), *Roseiflexus castenholzii* (YP 001433009.1) or *Roseiflexus* sp. (YP_001277512.1), and in alpha-proteobacteria as *Erythrobacter* sp. (WP_007163680), and as gamma proteobacteria (WP_009019528.1, WP_007234918.1, WP_009021869.1, WP 009470571.1), and can be obtained from thermoacidophilic archaea as *Crenarchaeotes Sulfolobus tokodaii* (NP_378167.1), *Acidianus hospitalis* (YP_004459517.1), *Metallosphaera cuprina* (YP_004410014.1) *Metallosphaera sedula* (YP_001190808.1), *Sulfolobus solfataricus* (NP_343563.1), *Metallosphaera yellowstonensis* (WP_009071519.1), *Sulfolobus islandicus* (YP_002844727.1; YP 002833533.1; YP 002830795.1), *Sulfolobus acidocaldarius* (YP_256941.1; YP 256733.1) and as *Archaeoglobus profundus* (YP_003401535.1), and as *Candidatus Chloracidobacterium thermophilum* (YP_004863680.1) or *Caldiarchaeum subterraneum* (BAJ47902.1).

Acetyl CoA carboxylase (EC 1.2.1.75) belongs to the group of biotin dependent carboxylases and can be obtained from bacteria as green non-sulfur phototrophic bacteria (Chloroflexi) as *Chloroflexus aurantiacus* (YP_001635254.1-55.1; YP_001637306.1; YP_001636995.1; YP_001634995.1), or carboxydotrophic acetogens as *C. ljungdahlii* (NC_014328.1-33.1).

In one embodiment, the microorganism comprises one or more exogenous nucleic acids adapted to increase expression of one or more nucleic acids native to the parental microorganism and which one or more nucleic acids encode one or more of the enzymes (or one or more subunits thereof) referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or Phosphotransacetylase/Acetate kinase operon promoters. It will be appreciated by those of skill in the art that other promoters which can direct expression, preferably a high level of expression under appropriate fermentation conditions, would be effective as alternatives to the exemplified embodiments. When a promoter is in a position such that it drives expression of a downstream coding sequence it is referred to as operably linked.

In one embodiment, the microorganism comprises one or more exogenous nucleic acids encoding and adapted to express one or more of the enzymes (or one or more subunits thereof) referred to herein before. In one embodiment, the microorganisms comprise one or more exogenous nucleic acid encoding and adapted to express at least two of the enzymes (or one or more subunits thereof).

In one particular embodiment, the microorganism comprises one or more exogenous nucleic acids encoding Malonyl-CoenzymeA reductase or a functionally equivalent variant thereof. In one particular embodiment, the microorganism comprises one or more exogenous nucleic acids encoding Acetyl CoA carboxylase or a functionally equivalent variant thereof. Acetyl CoA carboxylase may be comprised of 4 subunits, with each subunit encoded by a different gene. These genes may be combined in a single nucleic acid or two or more nucleic acids which together encode the whole enzyme. In addition, a particular parental microorganism may contain genes for only one, two, or three of these subunits. Accordingly, the invention encompasses engineering the microorganism using one or more exogenous nucleic to express one, two or three of the subunits only. Similarly, it encompasses engineering the microorganism to over-express one or more of the subunits if the genes are native to the microorganism. Combinations of over-expression of native subunit genes and introduction of any missing subunit genes is also envisaged.

In one embodiment, the Malonyl-CoenzymeA reductase is encoded by a nucleic acid comprising SEQ ID NO: 1, or a functionally equivalent variant thereof. In one embodiment, the Acetyl CoA carboxylase is encoded by one or more nucleic acid comprising SEQ ID NO: 18, 19, 20 and 21, or a functionally equivalent variant of any one or more thereof. Alternatively, the enzymes may be encoded by a nucleic acid sequence as described in a publicly available database, for example, as listed herein before.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination.

The exogenous nucleic acids may remain extra-chromosomal upon transformation of the parental microorganism or may integrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes (or one or more subunits thereof) as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

In one embodiment, the parental microorganism is selected from the group of anaerobic acetogens.

In one particular embodiment, the parental microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kiuvi.*

In one particular embodiment, the parental microorganism is selected from the cluster of ethanologenic, acetogenic Clostridia comprising the species *C. autoethanogenum, C. ljungdahlii,* and *C. ragsdalei* and related isolates. These include but are not limited to strains *C. autoethanogenum* JAI-1$^T$ (DSM10061) [Abrini J, Naveau H, Nyns E-J: *Clostridium autoethanogenum,* sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in Clostridial rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. 2002, U.S. Pat. No. 6,368,819], *C. ljungdahlii* O-52 (ATCC 55989) [Gaddy J L, Clausen E C, Ko C-W: Microbial process for the preparation of acetic acid as well as solvent for its extraction from the fermentation broth. 2002, U.S. Pat. No. 6,368,819], *C. ragsdalei* P11$^T$ (ATCC BAA-622) [Huhnke R L, Lewis R S, Tanner R S: Isolation and Characterization of novel Clostridial Species. International patent 2008, WO 2008/028055], related isolates such as "*C. coskatii*" [Zahn et al—Novel ethanologenic species *Clostridium coskatii* (US Patent Application number US20110229947)] and "*Clostridium* sp." (Tyurin et al., 2012, *J. Biotech Res.* 4: 1-12), or mutated strains such as *C. ljungdahlii* OTA-1 (Tirado-Acevedo O. Production of Bioethanol from Synthesis Gas Using *Clostridium ljungdahlii.* PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel Clostridial Species. International patent 2008, WO 2008/028055].

All species of this cluster have a similar morphology and size (logarithmic growing cells are between 0.5-0.7×3-5 µm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species.

International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Indole production was observed with all three species as well. However, the species differentiate in substrate utilization of various sugars (e.g., rhamnose, arabinose), acids (e.g., gluconate, citrate), amino acids (e.g., arginine, histidine), or other substrates (e.g., betaine, butanol). Moreover some of the species were found to be auxotrophic for certain vitamins (e.g., thiamine, biotin) while others were not.

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes encoding Malonyl-coenzymeA reductase or Acetyl CoA carboxylase (or one or more subunit thereof).

Nucleic Acids

The invention also provides nucleic acids and nucleic acid constructs of use in generating a recombinant microorganism of the invention.

In one embodiment, the nucleic acids comprise one or more sequences encoding one or more of the enzymes (or one or more subunits thereof) in the 3-HP biosynthesis pathway which when expressed in a microorganism allows the microorganism to produce 3-HP by fermentation of substrate comprising CO and/or $CO_2$. In one particular embodiment, the invention provides a nucleic acid encoding two or more enzymes (or one or more subunits thereof) which when expressed in a microorganism allows the microorganism to produce 3-HP by fermentation of substrate comprising CO and/or $CO_2$.

In one particular embodiment, the enzymes are chosen from Malonyl CoA reductase, Acetyl CoA carboxylase and a functionally equivalent variant of any one or more thereof.

In one embodiment, a nucleic acid of the invention comprises one or more nucleic acid sequences encoding Malonyl-CoenzymeA reductase, Acetyl CoA carboxylase or a functionally equivalent variant of any one or more thereof, in any order.

In one embodiment, a nucleic acid of the invention comprises one or more nucleic acid sequences encoding one or more subunit of Acetyl CoA carboxylase or a functionally equivalent variant of any one or more thereof, in any order.

Exemplary amino acid sequences and nucleic acid sequence encoding each of the above enzymes are provided herein or can be obtained from GenBank as mentioned hereinbefore. However, skilled persons will readily appreciate alternative nucleic acids sequences encoding the enzymes or functionally equivalent variants thereof, having regard to the information contained herein, in GenBank and other databases, and the genetic code.

In one embodiment, Malonyl-CoenzymeA reductase has a sequence as herein before described or is a functionally equivalent variant thereof.

In one embodiment, the nucleic acid sequence encoding Acetyl CoA carboxylase has a sequence as herein before described or is a functionally equivalent variant thereof.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kinase promoter is used. In another embodiment a pyruvate: ferredoxin oxidoreductase promoter, an Rnf complex operon promoter or an ATP synthase operon promoter. In one particular embodiment, the promoter is from *C. autoethanogenum*.

The nucleic acids of the invention may remain extrachromosomal upon transformation of a parental microorganism or may be adapted for integration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques known in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps: introduction into a shuttle microorganism of (i) of an expression construct/vector as described herein and (ii) a methylation construct/vector comprising a methyltransferase gene; expression of the methyltransferase gene; isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism that facilitates the methylation of the nucleic acid sequences that make up the expression construct/vector. In a particular embodiment, the shuttle microorganism is a restriction negative *E. coli*, *Bacillus subtilis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ ID NO: 6, or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ ID NO: 26, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used (for example, SEQ ID NO: 7).

Methods of Production

The invention provides a method for the production of 3-HP and optionally one or more other products by microbial fermentation comprising fermenting a substrate comprising CO and/or $CO_2$ using a recombinant microorganism of the invention. Preferably, 3-HP is the main fermentation product. The methods of the invention may be used to reduce the total atmospheric carbon emissions from an industrial process.

Preferably, the fermentation comprises the steps of anaerobically fermenting a substrate in a bioreactor to produce at least 3-HP using a recombinant microorganism of the invention.

In one embodiment the method comprises the steps of:
(a) providing a substrate comprising CO and/or $CO_2$ to a bioreactor containing a culture of one or more microorganism of the invention; and
(b) anaerobically fermenting the culture in the bioreactor to produce at least 3-HP.

In one embodiment the method comprises the steps of:
(a) capturing CO- and/or $CO_2$-containing gas produced as a result of the industrial process, before the gas is released into the atmosphere;
(b) the anaerobic fermentation of the CO- and/or $CO_2$-containing gas to produce the at least 3-HP by a culture containing one or more microorganism of the invention.

In one embodiment, the substrate comprises CO. In one embodiment, the substrate comprises $CO_2$ and CO. In another embodiment, the substrate comprises $CO_2$ and $H_2$. In another embodiment, the substrate comprises $CO_2$ and CO and $H_2$.

In one particular embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

In particular embodiments of the invention, the gaseous substrate fermented by the microorganism is a gaseous substrate comprising CO2 and H2. The CO2/H2 containing substrate may be a waste gas obtained as a by-product of an industrial process. In certain embodiments the industrial process is selected from the group consisting of hydrogen production. In certain embodiments the gaseous substrate comprising CO2 and H2 may be a blended gas stream, wherein at least a portion of the gas stream is derived from one or more industrial process is blended with at least a portion of CO2 or H2 to optimise the CO2:H2 ratio of the gaseous substrate. This may be particularly beneficial for industrial gas streams rich in either CO2 or H2. Examples of industrial process which produce by-product gas streams which can be used as a source for a CO2 and H2 substrate, or a CO2 and H2 blended substrate include coke manufacturing, refinery processes, ammnia production processes, methanol production processes, acetic acid production, natural gas refineries and power plants.

It will be appreciated that for growth of the bacteria and conversion of gas to products comprising 3-HP to occur, a suitable liquid nutrient medium in addition to the CO- and/or $CO_2$-containing substrate gas will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce one or more products using CO and/or $CO_2$ are known in the art. For example, suitable media are described Biebel (2001). In one embodiment of the invention the media is as described in the Examples section herein after.

The fermentation should desirably be carried out under appropriate conditions for the fermentation supporting the conversion of the gas to products comprising 3-HP to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO and/or $CO_2$ in the liquid phase does not become limiting, and maximum product concentrations to avoid product inhibition.

In addition, it is often desirable to increase the CO and/or $CO_2$ concentration of a substrate stream (or CO and/or $CO_2$ partial pressure in a gaseous substrate) and thus increase the efficiency of fermentation reactions where CO and/or $CO_2$ is a substrate. Operating at increased pressures allows a significant increase in the rate of CO and/or $CO_2$ transfer from the gas phase to the liquid phase where it can be taken up by the micro-organism as a carbon source to make products comprising 3-HP. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO- and/or $CO_2$-to-at least 3-HP conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO and/or $CO_2$-containing gaseous substrate is such as to ensure that the concentration of CO and/or $CO_2$ in the liquid phase does not become limiting. This is because a consequence of CO- and/or $CO_2$-limited conditions may be that one or more product is consumed by the culture.

The composition of gas streams used to feed a fermentation reaction can have a significant impact on the efficiency and/or costs of that reaction. For example, $O_2$ may reduce the efficiency of an anaerobic fermentation process. Processing of unwanted or unnecessary gases in stages of a fermentation process before or after fermentation can increase the burden on such stages (to products comprising where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173, 429 and 5,593,886 and WO 02/08438, and as described in the Examples section herein after.

3-HP, or a mixed stream containing 3-HP and/or one or more other products, may be recovered from the fermentation broth by methods known in the art, such as fractional distillation or evaporation, pervaporation, gas stripping and extractive fermentation, including for example, liquid-liquid extraction.

In certain preferred embodiments of the invention, 3-HP and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

3-HP may be recovered following fermentation using any appropriate methodology including but not limited to pervaporation, reverse osmosis, and liquid liquid extraction techniques.

EXAMPLES

The invention will now be described in more detail with reference to the following non-limiting examples.

Example 1

Two $CO_2$ fixing pathways, the linear Wood-Ljungdahl pathway of acetogens and the 3-HP cycle found in Green nonsulfur bacteria and Archea (Thauer, 2007, Science, 318: 1732-33) were combined to present a sustainable route towards the platform chemical 3-Hydroxypropionate (3-HP). This route allows fixation of 3 molecules of CO or $CO_2$ into one molecule of 3-HP. A carboxydotrophic acetogenic organism, *Clostridium autoethanogenum*, was chosen and metabolically engineered with genes performing the initial $CO_2$ fixation step from the nonsulfur photosynthetic bacterium *Chloroflexus auranticus* (FIG. 1).

Carboxydotrophic acetogens such as *Clostridium autoethanogenum* or *Clostridium ljungdahlii* are able to grow autotropically by fixing two molecules of CO or $CO_2$ and fusing them to form acetyl-CoA. Nonsulfur photosynthetic bacterium such as *Chloroflexus auranticus* are able to fix $CO_2$ in a cyclic process. They use acetyl-CoA as starting point and fuse it in an ATP dependent step catalyzed by an acetyl-CoA carboxylase (EC. 6.4.1.2) to form malonyl-CoA, which can then be reduced to 3-HP, the central intermediate of this cycle by action of a Malonyl-Coenzyme A reductase (EC 1.2.1.75) (Huegler et al, 2002, *J. Bacteriol.* 184: 2404-10). A Malonyl-Coenzyme A reductase gene, enzyme (GI: 163848165, Caur_2614; YP_001636209.1), was introduced into the carboxydotrophic organism to form a new metabolic route that fixes three molecules of CO or $CO_2$ into 3-HP. An acetyl-CoA carboxylase was identified to be already present in the host organisms as part of fatty acid biosynthesis (*C. autoethanogenum*: SEQ ID NO: 18-21; *C. ljungdahlii*: CLJU c42100-40, GI: 9447826-31, NC_014328.1-33.1) but the *Cloroflexus auranticus* acetyl-CoA carboxylase (GI: 163847210-11, Caur 1647-48, YP_001635254.1-55.1; GI:163849262, Caur 3739, YP_001637306.1; GI:163848951, Caur_3421, YP_001636995.1; GI:163846951, Caur_1378, YP 001634995.1) can be introduced in addition to the essential Malonyl-Coenzyme A reductase.

Materials and Methods

Microorganisms and Growth Conditions

C. autoethanogenum DSM23693 is a derivative of C. autoethanogenum DSM10061 sourced from DSMZ (The German Collection of Microorganisms and Cell Cultures, Inhoffenstraβe 7 B, 38124 Braunschweig, Germany).

E. coli XL1-Blue MRF' Kan was purchased from Stratagene (Santa Clara, Calif. 95051-7201, USA).

E. coli was cultivated under aerobic conditions, while all other strains were grown strictly anaerobically in a volume of 50 ml liquid media in serum bottles with fructose (heterotrophic growth) or 30 psi CO-containing steel mill gas (collected from New Zealand Steel site in Glenbrook, NZ; composition: 44% CO, 32% $N_2$, 22% $CO_2$, 2% $H_2$) in the headspace (autotrophic growth).

Media were prepared using standard anaerobic techniques (Hungate RE: A roll tube method for cultivation of strict anaerobes, in Norris J R and Ribbons D W (eds.), Methods in Microbiology, vol. 3B. Academic Press, New York, 1969: 117-132; Wolfe R S: Microbial formation of methane. *Adv Microb Physiol* 1971, 6: 107-146) according to formulations are given in Tab. 1-3. For solid media, 1.2% Bacto agar (B D, Frankton Lakes, N.J. 07417, USA) was added.

All strains were grown at 37° C. except as otherwise stated.

TABLE 1

PETC-MES medium (*C. autoethanogenum* pH 5.6)

| Media component | Concentration per 1.0 L of media |
| --- | --- |
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.2 g |
| $CaCl_2$ | 0.02 g |
| Trace metal solution (see below) | 10 ml |
| Wolfe's vitamin solution (see below) | 10 ml |
| Yeast Extract | 2 g |
| Resazurin (2 g/L stock) | 0.5 ml |
| 2-(N-morpholino)ethanesulfonic acid (MES) | 20 g |
| Sodium acetate | 0.25 g |
| Reducing agent | 0.006-0.008% (v/v) |
| Fructose (for heterotrophic growth) | 5 g |

| Trace metal solution | per L of stock |
| --- | --- |
| Nitrilotriacetic Acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |

| Reducing agent stock | per 100 mL of stock |
| --- | --- |
| NaOH | 0.9 g |
| Cystein•HCl | 4 g |
| $Na_2S$ | 4 g |

TABLE 2

Luria Bertani medium LB (*E. coli*)

| Media component | Concentration per 1.0 L of media |
| --- | --- |
| Tryptone | 10 g |
| Yeast Extract | 5 g |
| NaCl | 10 g |

TABLE 3

M9 minimal media (*E. coli*)

| Media component | Concentration per 1.0 L of media |
| --- | --- |
| $Na_2HPO_4$ | 6 g |
| $KH_2PO_4$ | 3 g |
| NaCl | 0.5 g |
| $NH_4Cl$ | 1 g |
| 100 mM $MgSO_4$ | 10 ml |
| Glucose | 20% |
| $CaCl_2$ | 10 mM |
| Thiamine-HCl | 100 mM |

Construction of Expression Plasmid with Malonyl-Coenzyme A Reductase from *C. aurantiacus*

Standard recombinant DNA and molecular cloning techniques were used (Sambrook, J., and Russell, D., Molecular cloning: A Laboratory Manual 3rd Ed., Cold Spring Harbour Lab Press, Cold Spring Harbour, N.Y., 2001). The DNA sequence of Malonyl-Coenzyme A reductase from *C. aurantiacus* was obtained from NCBI GenBank (GI:163848165, Caur_2614; YP 001636209.1).

The Malonyl-Coenzyme A reductase from *Chloroflexus aurantiacus* was codon-optimised (SEQ ID NO: 1) and synthesized by ATG:Biosynthetics GmbH (Merzhausen, Germany), flanked by NdeI and EcoI restriction sites for further sub-cloning. The Phosphotransacetylase/Acetate kinase operon promoter ($P_{pta-ack}$) of *C. autoethanogenum* was used for expression of Malonyl-Coenzyme A reductase. All DNA sequences used are given in Table 4.

TABLE 4

Sequences used for expression plasmid with Malonyl-Coenzyme A reductase from *C. aurantiacus*

| Description | Source | SEQ ID NO: |
| --- | --- | --- |
| Malonyl-Coenzyme A reductase | Codon-optimised | 1 |
| Phosphotransacetylase/Acetate kinase operon promoter region | *Clostridium autoethanogenum* DSM10061 | 2 |

The promoter region of the phosphotransacetylase-acetate kinase operon ($P_{pta-ack}$) (SEQ ID NO: 17) was amplified using primers Ppta-ack-NotI-F (SEQ ID NO: 8: GAGCG-GCCGCAATATGATATTTATGTCC) and Ppta-ack-NdeI-R (SEQ ID NO: 9: TTCCATATGTTTCATGTTCATTTC-CTCC) and cloned into the *E. coli-Clostridium* shuttle vector pMTL 85141 (FJ797651.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] using NotI and NdeI restriction sites and strain XL1-Blue MRF' Kan.

The antibiotic resistance gene in the created plasmid pMTL 85145 was subsequently replaced with an erythromycin resistance gene from pMTL 82254 (FJ797646.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] using FseI and PmeI restriction sites and strain XL1-Blue MRF' Kan. The created plasmid pMTL 85245 (SEQ ID NO: 3) and a 1625 by fragment of the repL gene from pMTL83151 (FJ797647.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] were both cut with FseI and AscI. A ligation was performed resulting in plasmid pMTL83245.

The created plasmid pMTL 83245 (SEQ ID NO: 4) and the 3660 by codon-optimised product of the Malonyl-Coenzyme A reductase gene were both cut with NdeI and EcoRI. A ligation was performed and ligation products were subsequently transformed into *E. coli* XL1-Blue MRF' Kan resulting in plasmid pMTL83245-SDR (SEQ ID NO: 5). DNA sequencing using oligonucleotides (given in Table 5) confirmed successful cloning of the Malonyl-Coenzyme A reductase gene without mutations.

TABLE 5

Primers used for confirmation of successful SDR cloning

| Oligonucleotide Name | DNA Sequence (5' to 3') | SEQ ID NO: |
|---|---|---|
| M13R | CAGGAAACAGCTATGAC | 10 |
| SDR_seqR1 | AGCAGCTTCTATCTGATCACCTGC | 11 |
| SDR_seqR2 | TGCTCTAATGCTGCTACGTCATTTG | 12 |
| SDR_seqR3 | TGCAAGTTCACTCTGAATCATTGC | 13 |
| SDR_seqR4 | ACATGGTGCTGGTTCATGACTAG | 14 |
| SDR_seqR5 | TCTAGCACCAAGTTCTCTTGCTG | 15 |
| M13 (-21) | TGTAAAACGACGGCCAG | 16 |

Determination of Enzyme Activities

The recombinant strain containing the plasmid pMTL 83245-SDR was grown up in LB medium containing the appropriate antibiotics under aerobic conditions overnight. The cells were inoculated into fresh LB medium with an initial OD600 of 0.1. The cells were harvested at logarithmic phase (OD600~0.6), and centrifuged at 13,000×g and 4° C. for 10 mins. The cell pellet was washed twice with 100 mM Tris-HCl (pH 7.8) and resuspended in the same wash buffer containing protease inhibitor and mixed with 1.44 g of 100 µm glass beads. Tubes were chilled on ice for 5 min prior to disruption in a Mini Bead Beater (Biospec Products) through 5 cycles of 1 min beating at 5,000 rpm followed by 1 min on ice between cycles. After lysis, the sample was centrifuged (13,000×g, 4° C. for 10 mins) and the supernatant aliquoted and stored at −80° C. until analysis. Protein content of the extracts was determined using a commercial kit (Pierce® Microplate BCA Protein Assay Kit-Reducing Agent Compatible, Thermo Scientific).

Malonyl-CoA reductase activity was determined at 45° C. using the method reported by Hugler et al. (Hugler, M., Menendez, C., Schagger, H., Fuchs, G., 2002. Malonyl-coenzyme A reductase from *Chloroflexus aurantiacus*, a key enzyme of the 3-hydroxypropionate cycle for autotrophic CO2 fixation. J. Bacteriol. 184 (9), 2404-2410). For routine assays, the enzyme lysate was pre-incubated at 45° C. in 100 mM Tris-HCl buffer (pH 7.8), containing 3 mM 1,4-dithioerythritol, 2 mM $MgCl_2$, and 0.3 mM NADPH for 10 mins. The reaction was initiated by the addition of 0.3 mM malonyl-CoA. The amount of NADPH consumed was determined using a molar extinction coefficient ($\Delta\epsilon_{365}$) of $3400M^{-1}$ $cm^{-1}$. One unit of SDR activity was defined as the amount of enzyme required to oxidize 2 µmmol of NADPH to $NADP^+$ per min. To study the effect of temperature on the activity of SDR, the assay was also performed at 37° C.

Methylation of Expression Plasmid with Malonyl-Coenzyme a Reductase from *C. aurantiacus*

Methylation of the 3-HP expression plasmid pMTL83245-SDR was performed in vivo in *E. coli* using a synthesized hybrid Type II methyltransferase gene (SEQ ID NO: 6) designed from methyltransferase genes from *C. autoethanogenum*, *C. ragsdalei* and *C. ljungdahlii*. The methyltransferase (SEQ ID NO: 6) was synthesised and fused with an inducible lac promoter in vector pGS20 (ATG:biosynthetics GmbH, Merzhausen, Germany) (SEQ ID NO: 7).

Both expression plasmid and methylation plasmid were transformed into the same cells of restriction negative *E. coli* XL1-Blue MRF' Kan, which is possible due to their compatible Gram-(−) origins of replication (high copy ColE1 in expression plasmid and low copy p15A in methylation plasmid). In vivo methylation was induced by addition of 1 mM IPTG, and methylated plasmids were isolated using QIAGEN Plasmid Midi Kit (QIAGEN GmbH, Hilden, Germany). The resulting mixture was used for transformation experiments with *C. autoethanogenum* DSM23693, but only the abundant (high-copy) expression plasmid which has a Gram-(+) replication origin (repH) is able to replicate in Clostridia.

Transformation of Methylated 3-HP Expression Plasmid in *C. autoethanogenum*

To make competent cells of *C. autoethanogenum* DSM23693, a 50 ml culture (PETC media (Table 1) with steel mill gas and fructose as carbon source; 37° C.) was subcultured to fresh media for 3 consecutive days. These cells were used to inoculate 50 ml PETC media containing 40 mM DL-threonine at an $OD_{600nm}$ of 0.05. When the culture reached an $OD_{600nm}$ of 0.45, the cells were transferred into an anaerobic chamber and harvested at 4,700×g and 4° C. The culture was twice washed with ice-cold electroporation buffer (270 mM sucrose, 1 mM $MgCl_2$, 7 mM sodium phosphate, pH 7.4) and finally suspended in a volume of 600 µl fresh electroporation buffer. This mixture was transferred into a pre-cooled electroporation cuvette with a 0.4 cm electrode gap containing ~10 µg of the methylated plasmid mix. Since an additional Type I restriction system was identified in the genome of *C. ljungdahlii* compared to *C. autoethanogenum*, 1 µl of a Type I restriction inhibitor (EPICENTRE Biotechnologies, Madison, Wis. 53713, USA) was added to the plasmid mix. The cells were mixed with plasmid and restriction inhibitor and immediately pulsed using a Gene pulser Xcell electroporation system (Bio-Rad Laboratories, Hercules, Calif. 94547, USA) with the following settings: 2.5 kV, 600Ω, and 25 µF. Time constants were between 3.7-5.1 ms. For regeneration, the culture was transferred in 5 ml PETC-MES media (Table 1), which increased recovery of the cells. The culture was monitored at a wavelength of 600 nm using a Spectronic Helios Epsilon Spectrophotometer (Thermo Fisher Scientific Inc., Waltham Mass. 02454, USA) equipped with a tube holder. Once growth was observed (one doubling), the culture was scaled up to 10 ml and later 50 ml PETC-MES media containing each 5 μg/ml clarithromycin and 30 psi steel mill gas in the headspace as sole carbon source.

Analysis of Metabolites

HPLC analysis of 3-hydroxypropionate (3-HP) and other metabolites was performed using an Agilent 1100 Series HPLC system equipped with a RID (Refractive Index Detector) operated at 35° C. and an Aminex HPX-87H column (300×7.8 mm, particle size 5 μm) kept at 35° C. Slightly acidified water was used (0.005 M $H_2SO_4$) as mobile phase with a flow rate of 0.6 ml/min. To remove proteins and other cell residues, 400 μl samples were mixed with 100 μl of a 1% (w/v) 5-Sulfosalicylic acid in 1M sulphuric acid and centrifuged at 14,000 rpm for 3 min to separate precipitated residues. 10 μl of the supernatant were then injected into the HPLC for analyses.

Results

Production of 3-HP in Transformed Cells

3-HP Production from CO and $CO_2/H_2$ with *C. aurantiacus* Pathway Genes in *C. autoethanogenum*:

Growth experiments were carried out with transformed *C. autoethanogenum* DSM23693 carrying plasmid pMTL83245-SDR in 50 ml PETC-MES media (Table 1; without fructose) in serum with rubber stoppers and 30 psi steel mill gas (collected from New Zealand Steel site in Glenbrook, NZ; composition: 44% CO, 32% $N_2$, 22% $CO_2$, 2% $H_2$) in the headspace as sole energy and carbon source. 3-HP production was confirmed using HPLC analysis.

Example 2

Improving 3-HP Production Via Increasing Biotin Biosynthesis

Fixation of CO2 onto acetyl-CoA by acetyl-CoA carboxylase (ACC) is mediated by biotin (vitamin B7, vitamin H). Biotin is required as co-factor for this carboxylation reaction.

Acetyl-CoA carboxylase is a complex consisting of four different subunits, AccA, AccB, AccC, and AccD, where biotin is covalently bound to subunit AccB. Carboxylation of biotin is catalyzed by subunit AccC with the expense of ATP. The subsequent transfer of $CO_2$ from carboxylated biotin to acetyl-CoA by AccA and AccD results in formation of malonyl-CoA. In the first step of the activation of the acetyl-CoA carboxylase complex, the binding of biotin to AccB is catalyzed by biotin-[acetyl-CoA carboxylase] ligase (holoenzyme synthetase).

To improve CO2 fixation and 3-HP production via acetyl-CoA carboxylase in carboxydotrophic acetogens, the pool of biotin co-factor can be increased by over-expression of genes involved in the biosynthesis pathway of this co-factor. Biotin biosynthesis includes enzymes 6-carboxyhexanoate-CoA ligase [EC:6.2.1.14], 8-amino-7-oxononanoate synthase [EC:2.3.1.47], adenosylmethionine-8-amino-7-oxononanoate aminotransferase [EC:2.6.1.62], biotin synthetase [EC:2.8.1.6], biotin-[acetyl-CoA-carboxylase] ligase [EC:6.3.4.15], biotinidase [EC:3.5.1.12], biotin-protein ligase [EC:6.3.4.15; EC:6.3.4.11; EC:6.3.4.10; EC:6.3.4.9], ethiobiotin synthetase [EC:6.3.3.3], type III pantothenate kinase [EC:2.7.1.33].

Example 3

Improving 3-HP Production Via Limiting Fatty Acid Biosynthesis

Malonyl-CoA is also a precursor for fatty acid biosynthesis. To increase 3-HP production, the rate of fatty acid biosynthesis can be limited in favour for 3-HP production. A malonyl-CoA:acyl carrier protein transacylase (FabD) [EC: 2.3.1.39] initiates the elongation of fatty acid chains. The gene encoding this enzyme can be downregulated or activity of this enzyme decreased to prevent malonyl-CoA from being used for the native fatty acid biosynthesis.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise," "comprising" and the like, are to be construed in an inclusive sense as opposed to an exclusive sense, that is to say, in the sense of "including, but not limited to."

We claim:

1. A recombinant carboxydotrophic, acetogenic bacterium comprising two gas-fixing fermentation pathways, including a Wood-Ljungdahl pathway capable of converting 2 molecules of CO or $CO_2$ into one molecule of acetyl-CoA and a 3-hydroxypropionate biosynthesis pathway capable of converting 1 molecule of $CO_2$ and 1 molecule of acetyl-CoA into 1 molecule of 3-hydroxypropionate, wherein the 3-hydroxypropionate biosynthesis pathway comprises an acetyl-CoA carboxylase (EC 6.4.1.2) and a malonyl-CoA reductase (EC 1.2.1.75), wherein at least the malonyl-CoA reductase is exogenous to the bacterium, and wherein the bacterium is derived from a parental bacterium selected from the group consisting of Clostridium autoethanogenum, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchi, Blautia producta, Eubacterium limosum, Moorella thermoacetica, Moorella thermoautotrophica, Sporomusa ovata, Sporomusa silvacetica, Sporomusa sphaeroides, Oxobacter pfennigii, and Thermoanaerobacter kivui.

2. The recombinant carboxydotrophic, acetogenic bacterium of claim 1, wherein the bacterium is capable of producing 3-hydroxypropionate from a gaseous substrate comprising CO and/or $CO_2$.

3. The recombinant carboxydotrophic, acetogenic bacterium of claim 2, wherein the gaseous substrate is an industrial waste gas or syngas.

4. The recombinant carboxydotrophic, acetogenic bacterium of claim 1, wherein the malonyl-CoA reductase is encoded by a nucleic acid codon optimized for expression in the bacterium.

5. The recombinant carboxydotrophic, acetogenic bacterium of claim 1, wherein the malonyl-CoA reductase is at least 85% identical to the amino acid sequence encoded by the nucleotide sequence of SEQ ID NO: 1.

6. The recombinant carboxydotrophic, acetogenic bacterium of claim 1, wherein the malonyl-CoA reductase is at least 95% identical to the amino acid sequence encoded by the nucleotide sequence of SEQ ID NO: 1.

7. The recombinant carboxydotrophic, acetogenic bacterium of claim 1, wherein the malonyl-CoA reductase is derived from Chloroflexus aurantiacus.

8. The recombinant carboxydotrophic, acetogenic bacterium of claim 1, wherein the bacterium is derived from a parental bacterium selected from the group consisting of Clostridium autoethanogenum and Clostridium ragsdalei.

9. The recombinant carboxydotrophic, acetogenic bacterium of claim 1, wherein the acetyl-CoA carboxylase is encoded by a nucleic acid codon optimized for expression in the bacterium.

10. The recombinant carboxydotrophic, acetogenic bacterium of claim 1, wherein the acetyl-CoA carboxylase is derived from a member of the genus Clostridium, Metallosphaera, Sulfolobus, or Choroflexus.

11. The recombinant carboxydotrophic, acetogenic bacterium of claim 1, wherein the acetyl-CoA carboxylase is derived from Clostridium ljungdahlii or Chloroflexus aurantiacus.

12. A process for producing 3-hydroxypropionate comprising culturing the recombinant carboxydotrophic, acetogenic bacterium of claim 1 in the presence of a gaseous substrate comprising CO and/or $CO_2$.

13. The process of claim 12, wherein the gaseous substrate is an industrial waste gas or syngas.

* * * * *